(12) United States Patent
Andree et al.

(10) Patent No.: US 6,992,044 B1
(45) Date of Patent: Jan. 31, 2006

(54) SUBSTITUTED PHENYLURACILS

(75) Inventors: Roland Andree, Langenfeld (DE); Hans-Georg Schwarz, Langenfeld (DE); Udo Schneider, Leverkusen (DE); Ralf Wischnat, Köln (DE); Mark Wilhelm Drewes, Langenfeld (DE); Peter Dahmen, Neuss (DE); Dieter Feucht, Monheim (DE); Rolf Pontzen, Leichlingen (DE)

(73) Assignee: Bayer CropScience AG, Monheim (DE)

( * ) Notice: Subject to any disclaimer, the term of this patent is extended or adjusted under 35 U.S.C. 154(b) by 247 days.

(21) Appl. No.: 10/399,359

(22) PCT Filed: Oct. 8, 2001

(86) PCT No.: PCT/EP01/11589

§ 371 (c)(1),
(2), (4) Date: Aug. 18, 2003

(87) PCT Pub. No.: WO02/34725

PCT Pub. Date: May 2, 2002

(30) Foreign Application Priority Data

Oct. 20, 2000 (DE) ................................ 100 51 981

(51) Int. Cl.
*A01N 43/00* (2006.01)
*A01N 43/72* (2006.01)
*A01N 43/64* (2006.01)
*A01N 43/60* (2006.01)
*A01N 43/58* (2006.01)

(52) U.S. Cl. ................. 504/129; 504/131; 504/133; 504/136; 504/137; 540/524; 544/55; 544/96; 544/180; 544/182; 544/295; 544/296; 544/310

(58) Field of Classification Search ................ 504/129, 504/131, 133, 136, 137; 540/524; 544/55, 544/96, 180, 182, 295, 296, 310
See application file for complete search history.

(56) References Cited

U.S. PATENT DOCUMENTS

| 4,191,775 | A |   | 3/1980  | Glen ........................ 424/304 |
| 4,979,982 | A |   | 12/1990 | Brouwer et al. ............... 71/92 |
| 5,017,211 | A | * | 5/1991  | Wenger et al. ................ 71/92 |
| 5,084,084 | A |   | 1/1992  | Satow et al. .................. 71/92 |
| 5,127,935 | A |   | 7/1992  | Satow et al. .................. 71/92 |
| 5,154,755 | A |   | 10/1992 | Satow et al. .................. 71/92 |
| 5,169,430 | A |   | 12/1992 | Strunk et al. ................. 71/92 |
| 5,183,492 | A |   | 2/1993  | Suchy et al. ................ 504/243 |
| 5,356,863 | A |   | 10/1994 | Satow et al. ............... 504/243 |
| 5,593,945 | A |   | 1/1997  | Andree et al. .............. 504/243 |
| 5,681,794 | A |   | 10/1997 | Andree et al. .............. 504/243 |
| 5,798,316 | A | * | 8/1998  | Theodoridis ............... 504/136 |
| 5,972,951 | A |   | 10/1999 | Gaster et al. ............... 514/278 |
| 6,110,870 | A |   | 8/2000  | Andree et al. .............. 504/243 |

FOREIGN PATENT DOCUMENTS

| CA | 2336762     |   | 1/2000  |
| DE | 195 24 617  | * | 1/1997  |
| GB | 1 503 244   |   | 9/1979  |
| WO | 97/01541    |   | 1/1997  |
| WO | 97/02253    |   | 1/1997  |
| WO | 98/41093    |   | 9/1998  |
| WO | 98/50358    |   | 11/1998 |

OTHER PUBLICATIONS

J. Heterocycl. Chem., Jun. 9, 1972, pp. 513-522, Albert W. Lutz and Susan H. Trotto, "Novel 6-(Trifluoromethyl)cytosines and 6-(Trifluoromethyl)uracils".

Database Crossfire Beilstein 'Online! Beilstein Institut zur Förderung der Chemischen Wissen-schaften, Frankfurt am Main, DE: Database accession No. 775149 XP002190606 Zusammenfassung & Okamoto et al.: Bull. Chem. Soc. JPN, Bd. 60, Nr. 11,—1987 pp. 3999-4004, Tokyo.

(Continued)

*Primary Examiner*—James O. Wilson
*Assistant Examiner*—Zachary C. Tucker
(74) *Attorney, Agent, or Firm*—Richard E.L. Henderson

(57) ABSTRACT

The invention relates to novel substituted phenyl uracils of the formula (I)

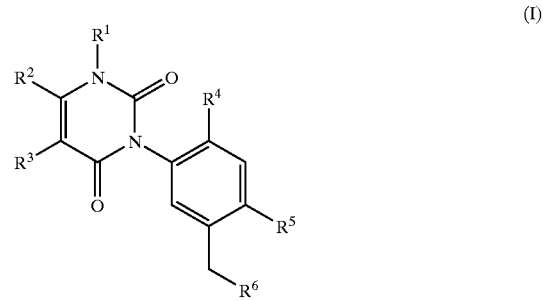

in which
$R^1$ represents hydrogen, amino or in each case optionally substituted alkyl, alkenyl or alkynyl,
$R^2$ represents cyano, carboxy, carbamoyl, thiocarbamoyl or optionally substituted alkyl or alkoxycarbonyl,
$R^3$ represents hydrogen, halogen or optionally substituted alkyl,
$R^4$ represents hydrogen, nitro, cyano, alkoxy or halogen,
$R^5$ represents cyano, thiocarbamoyl, halogen or optionally substituted alkyl or alkoxy and
$R^6$ represents an optionally substituted nitrogen-containing heterocyclic group which is attached to $R^6$ via N,
to processes for their preparation, to their use as crop treatment agents, and to intermediates and processes for their preparation.

14 Claims, No Drawings

OTHER PUBLICATIONS

Database Crossfire Beilstein 'Online! Beilstein Institut zur Förderung der Chemischen Wissen-schaften, Frankfurt am Main, DE: 1989 Defoin, A. et al.: Database accession No. 636522 XP002190607 Zusammenfassung; Beispiele & Defoin A. et al.: Helv. Chim. Acta, Bd. 72,—1989 pp. 1199-1215.

Database Crossfire Beilstein 'Online! Beilstein Institut zur Förderung der Chemischen Wissen-schaften, Frankfurt am Main, DE; Kuhn et al.: Database accession No. 3337592 XP002190608 Zusammenfassung & Kuhn et al.: Chem. Ber., Bd. 68,—1935 pp. 1765-1770, Beispiele.

Database Crossfire Beilstein 'Online! Beilstein Institut zur Förderung der Chemischen Wissen-schaften, Frankfurt am Main, DE; Database accession No. 3275223 XP002190609 Zusammenfassung & Sahashi, et al.,: Proc. Imp. Acad. Tokyo, Bd. 21,—1945 pp. 44-50, Tokyo Beispiele.

* cited by examiner

SUBSTITUTED PHENYLURACILS

This application was filed under 35 U.S.C. 371 and is the U.S. national stage of PCT/EP01/11589, filed 8 Oct. 2001.

The present invention relates to novel substituted phenyl uracils, to processes for their preparation and to their use as crop treatment agents, in particular as herbicides.

It is already known that certain substituted phenyl uracils have herbicidal properties (cf. EP-A-408382/U.S. Pat. No. 5,084,084/U.S. Pat. No. 5,127,935/U.S. Pat. No. 5,154,755, EP-A-563384, EP-A-648749, U.S. Pat. No. 4,979,982, U.S. Pat. No. 5,169,430, WO-A-91/00278, WO-A-97/01541, WO-A-98/41093, WO-A-00/02866). However, these compounds have hitherto not attained any particular importance.

This invention, accordingly, provides the novel substituted phenyl uracils of the formula (I)

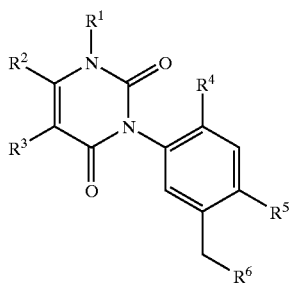

(I)

in which
$R^1$ represents hydrogen, amino or in each case optionally substituted alkyl, alkenyl or alkinyl,
$R^2$ represents cyano, carboxy, carbamoyl, thiocarbamoyl or in each case optionally substituted alkyl or alkoxy-carbonyl,
$R^3$ represents hydrogen, halogen or optionally substituted alkyl,
$R^4$ represents hydrogen, nitro, cyano, alkoxy or halogen,
$R^5$ represents cyano, thiocarbamoyl, halogen or in each case optionally substituted alkyl or alkoxy and
$R^6$ represents an optionally substituted nitrogen-containing heterocyclic grouping which is attached via N,
  including all possible tautomeric forms of the compounds of the general formula (I) and the possible salts or acid or base adducts of the compounds of the general formula (I)-.

In the definitions, the hydrocarbon chains, such as alkyl or alkanediyl, are in each case straight-chain or branched—including in combination with hetero atoms, such as in alkoxy.

Preferred substituents or preferred ranges of the radicals present in the formulae mentioned above and below are defined below.

$R^1$ preferably represents hydrogen, amino, optionally cyano-, halogen- or $C_1$–$C_4$-alkoxy substituted alkyl having 1 to 4 carbon atoms or in each case optionally halogen-substituted alkenyl or alkinyl having in each case 2 to 4 carbon atoms.

$R^2$ preferably represents cyano, carboxy, carbamoyl, thiocarbamoyl or in each case optionally cyano-, halogen- or $C_1$–$C_4$-alkoxy substituted alkyl or alkoxycarbonyl having in each case 1 to 4 carbon atoms.

$R^3$ preferably represents hydrogen, halogen or optionally halogen-substituted alkyl having 1 to 4 carbon atoms.

$R^4$ preferably represents hydrogen, nitro, cyano, $C_1$–$C_4$-alkoxy or halogen.

$R^5$ preferably represents cyano, thiocarbamoyl, halogen or in each case optionally halogen-substituted alkyl or alkoxy having in each case 1 to 4 carbon atoms.

$R^6$ preferably represents an optionally nitro-, hydroxyl-, mercapto-, amino-, cyano-, carboxyl-, carbamoyl-, halogen-, $C_1$–$C_4$-alkyl-, cyano-$C_1$–$C_4$-alkyl-, carboxy-$C_1$–$C_4$-alkyl-, $C_1$–$C_4$-halogenoalkyl-, $C_1$–$C_4$-alkoxy-$C_1$–$C_4$-alkyl-, $C_1$–$C_4$-alkoxy-carbonyl-$C_1$–$C_4$-alkyl-, $C_1$–$C_4$-alkylaminocarbonyl-$C_1$–$C_4$-alkyl-, di-($C_1$–$C_4$-alkyl)-aminocarbonyl-$C_1$–$C_4$-alkyl-, $C_1$–$C_4$-alkyl-carbonyl-, $C_1$–$C_4$-halogenoalkyl-carbonyl-, $C_1$–$C_4$-alkoxy-$C_1$–$C_4$-alkyl-carbonyl-, $C_1$–$C_4$-alkoxy-, cyano-$C_1$–$C_4$-alkoxy-, $C_1$–$C_4$-halogenoalkoxy-, $C_1$–$C_4$-alkoxy-$C_1$–$C_4$-alkoxy-, carboxy-$C_1$–$C_4$-alkoxy-, $C_1$–$C_4$-alkoxy-carbonyl-$C_1$–$C_4$-alkoxy-, $C_1$–$C_4$-alkylaminocarbonyl-$C_1$–$C_4$-alkoxy-, di-($C_1$–$C_4$-alkyl)-aminocarbonyl-$C_1$–$C_4$-alkoxy-, $C_1$–$C_4$-alkoxy-carbonyl, $C_2$–$C_4$-alkenyloxy-, $C_2$–$C_4$-alkinyloxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl-, $C_1$–$C_4$-alkyl-carbonyl-amino-, $C_1$–$C_4$-alkoxy-carbonyl-amino-, $C_1$–$C_4$-alkyl-sulphonyl-amino-, $C_2$–$C_4$-alkenyl-, $C_2$–$C_4$-halogenoalkenyl-, $C_2$–$C_4$-alkinyl-, $C_2$–$C_4$-alkenyloxy-, $C_2$–$C_4$-halogenoalkenyloxy-, $C_2$–$C_4$-alkinyloxy-, $C_2$–$C_4$-alkenylthio-, $C_2$–$C_4$-halogenoalkenylthio-, $C_2$–$C_4$-alkinylthio-, $C_2$–$C_4$-alkenylamino-, $C_2$–$C_4$-alkinylamino-, (in each case optionally halogen-substituted) $C_3$–$C_6$-cycloalkyl-, $C_3$–$C_6$-cycloalkyloxy-, $C_3$–$C_6$-cycloalkylthio-, $C_3$–$C_6$-cycloalkylamino-, $C_3$–$C_6$-cycloalkyl-$C_1$–$C_4$-alkyl-, $C_3$–$C_6$-cycloalkyl-$C_1$–$C_4$-alkyloxy-, $C_3$–$C_6$-cycloalkyl-$C_1$–$C_4$-alkylthio-, $C_3$–$C_6$-cycloalkyl-$C_1$–$C_4$-alkylamino-, (in each case optionally nitro-, cyano-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted) phenyl-, pyridyl-, phenyloxy-, phenylthio-, phenylamino-, benzyl-, benzyloxy-, benzylthio- or benzylamino-substituted 4- to 12-membered saturated or unsaturated monocyclic or bicyclic heterocyclic grouping which is attached via N and contains 1 to 4 hetero atoms selected from the following group: nitrogen atoms, oxygen atoms, sulphur atoms, —SO-groups, —SO$_2$-groups, —CO-groups and/or —CS-groups.

$R^1$ particularly preferably represents hydrogen, amino, or in each case optionally cyano, fluorine, chlorine, methoxy- or ethoxy-substituted methyl, ethyl, n- or i-propyl, or in each case optionally fluorine- and/or chlorine-substituted propenyl, butenyl, propinyl or butinyl.

$R^2$ particularly preferably represents cyano, carboxyl, carbamoyl, thiocarbamoyl or in each case optionally cyano-, fluorine-, chlorine-, methoxy- or ethoxy-substituted methyl, ethyl, n- or i-propyl, methoxycarbonyl, ethoxycarbonyl, n- or i-propoxy-carbonyl.

$R^3$ particularly preferably represents hydrogen, fluorine, chlorine, bromine or in each case optionally fluorine, and/or chlorine-substituted methyl, ethyl, n- or i-propyl.

$R^4$ particularly preferably represents hydrogen, methoxy, ethoxy, nitro, cyano, fluorine, chlorine or bromine.

$R^5$ particularly preferably represents cyano, thiocarbamoyl, fluorine, chlorine, bromine or in each case optionally fluorine- or chlorine-substituted methyl, ethyl, n- or i-propyl, methoxy, ethoxy, n- or i-propoxy.

$R^6$ particularly preferably represents an optionally nitro-, hydroxyl-, mercapto-, amino-, cyano-, carboxyl-, carbamoyl-, fluorine-, chlorine-, bromine-, iodine-, methyl-, ethyl-, n- or i-propyl, n-, i-, s- or t-butyl-, cyanomethyl-, cyanoethyl-, cyano-n-propyl-, cyano-i-propyl-, carboxymethyl-, carboxyethyl-, carboxy-n-propyl-, carboxy-i-propyl-, fluoromethyl, chloromethyl-, bromomethyl-, difluoromethyl-, dichloromethyl-, trifluoromethyl-, trichloromethyl-, fluorodichloromethyl-, chlorodifluoromethyl-, fluoroethyl-, chloroethyl-, difluoroethyl-, dichloroethyl-, chlorofluoroethyl-, trifluoroethyl-, trichloroethyl-, fluorodichloroethyl-, chlorodifluoroethyl-, tetrafluoroethyl-, chlorotrifluoroethyl-, dichlorodifluoroethyl-, pentafluoroethyl-, methoxymethyl-, ethoxymethyl-, n- or i-propoxymethyl-, methoxyethyl-, ethoxyethyl-, n- or i-propoxyethyl-, methoxypropyl-, ethoxypropyl-, methoxycarbonylmethyl-, ethoxycarbonylmethyl-, n- or i-propoxycarbonylmethyl-, methoxycarbonylethyl-, ethoxycarbonylethyl-, n- or i-propoxycarbonylethyl-, methoxycarbonylpropyl-, ethoxycarbonylpropyl-, methylaminocarbonylmethyl-, ethylaminocarbonylmethyl-, n- or i-propylaminocarbonylmethyl-, methylaminocarbonylethyl-, ethylaminocarbonylethyl, n- or i-propylaminocarbonylethyl, dimethylaminocarbonylmethyl-, dimethylaminocarbonylethyl-, acetyl-, propionyl-, n- or i-butyroyl-, trifluoroacetyl-, chloroacetyl-, dichloroacetyl-, trichloroacetyl-, methoxyacetyl-, ethoxyacetyl-, methoxy-, ethoxy-, n- or i-propoxy-, cyanomethoxy-, cyanoethoxy-, cyano-n-propoxy-, cyano-i-propoxy, fluoromethoxy-, difluoromethoxy-, trifluoromethoxy-, fluorodichloromethoxy-, chlorodifluoromethoxy-, fluoroethoxy-, chloroethoxy-, difluoroethoxy-, dichloroethoxy-, chlorofluoroethoxy-, trifluoroethoxy-, trichloroethoxy-, fluorodichloroethoxy-, chlorodifluoroethoxy-, methoxymethoxy-, ethoxymethoxy, n- or i-propoxymethoxy-, methoxyethoxy-, ethoxyethoxy-, n- or i-propoxyethoxy-, carboxymethoxy-, carboxyethoxy-, methoxycarbonylmethoxy-, ethoxycarbonylmethoxy-, n- or i-propoxycarbonylmethoxy-, methoxycarbonylethoxy-, ethoxycarbonylethoxy-, n- or i-propoxycarbonylethoxy-, methylaminocarbonylmethoxy-, ethylaminocarbonylmethoxy-, n- or i-propylaminocarbonylmethoxy-, methylaminocarbonylethoxy-, ethylaminocarbonylethoxy-, n- or i-propylaminocarbonylethoxy-, dimethylaminocarbonylmethoxy-, dimethylaminocarbonylethoxy-, methoxycarbonyl-, ethoxycarbonyl-, n- or i-propoxycarbonyl-, propenyloxy-, butenyloxy-, propinyloxy-, butinyloxy-, methylthio-, ethylthio-, n- or i-propylthio-, difluoromethylthio-, trifluoromethylthio-, fluorodichloromethylthio-, chlorodifluoromethylthio-, methylsulphinyl-, ethylsulphinyl-, n- or i-propylsulphinyl-, trifluoromethylsulphinyl-, methylsulphonyl-, ethylsulphonyl-, n- or i-propylsulphonyl-, trifluoromethylsulphonyl-, (in each case optionally fluorine, chlorine, methoxy- or ethoxy-substituted)acetylamino-, propionylamino-, n- or i-butyroylamino-, methoxycarbonylamino-, ethoxycarbonylamino-, n- or i-propoxycarbonylamino-, (in each case optionally fluorine- and/or chlorine-substituted) methylmethylsulphonylamino-, ethylsulphonylamino-, n- or i-propylsulphonylamino-, (in each case optionally fluorine- and/or chlorine-substituted) cyclopropyl-, cyclobutyl-, cyclopentyl-, cyclohexyl-, cyclopropyloxy-, cyclobutyloxy-, cyclopentyloxy-, cyclohexyloxy-, cyclopropylthio-, cyclobutylthio-, cyclopentylthio-, cyclohexylthio-, cyclopropylamino-, cyclobutylamino-, cyclopentylamino-, cyclohexylamino-, cyclopropylmethyl-, cyclobutylmethyl-, cyclopentylmethyl-, cyclohexylmethyl-, cyclopropylmethoxy-, cyclobutylmethoxy-, cyclopentylmethoxy-, cyclohexylmethoxy-, cyclopropylmethylthio-, cyclobutylmethylthio-, cyclopentylmethylthio-, cyclohexylmethylthio-, cyclopropylmethylamino-, cyclobutylmethylamino-, cyclopentylmethylamino-, cyclohexylmethylamino-, (in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted) phenyl-, pyridyl-, phenyloxy-, phenylthio-, phenylamino-, benzyl-, benzyloxy-, benzylthio- or benzylamino-substituted saturated or unsaturated monocyclic or bicyclic nitrogen-containing heterocyclic grouping, attached via N, from the group consisting of pyrrolyl, pyrrolidinyl, pyrazolyl, imidazolyl, isoxazolidinyl, triazolyl, piperidinyl, morpholinyl, thiomorpholinyl, piperazinyl, or represents one of the groupings below.

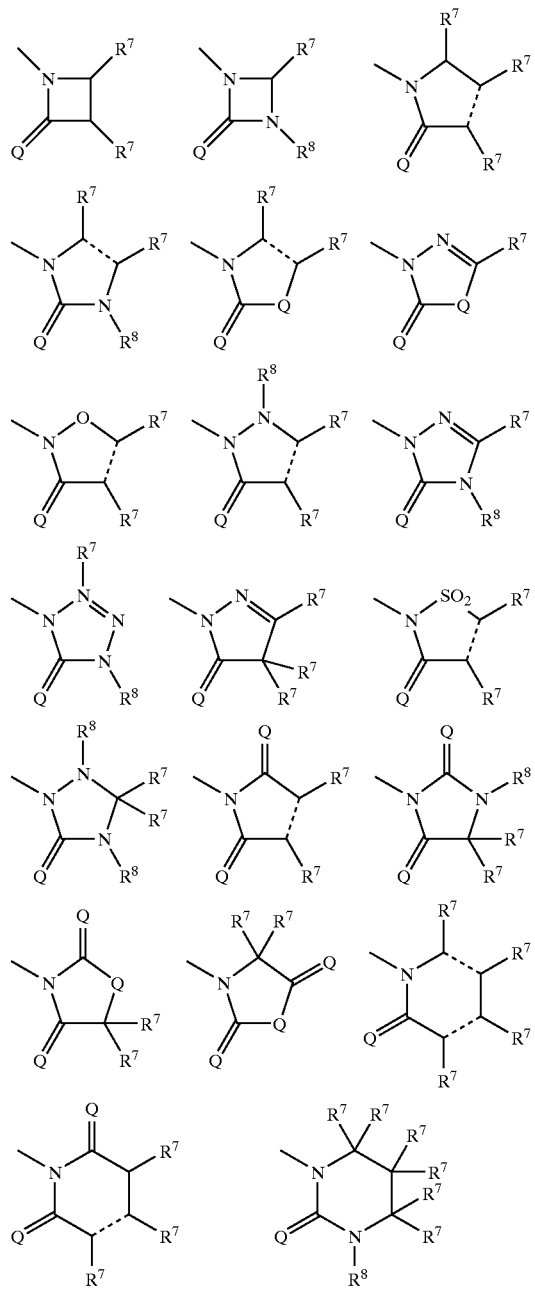

-continued

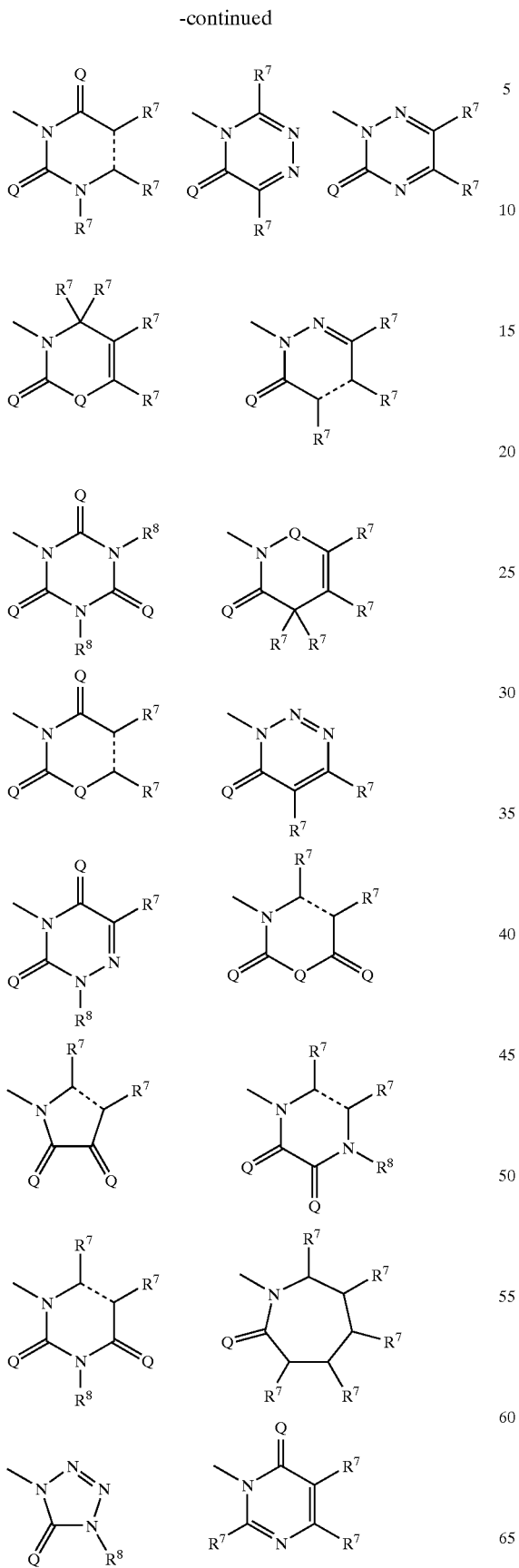

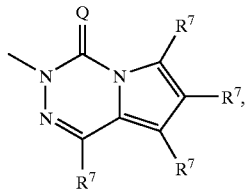

where each of the bonds, shown with a dashed line, is a single bond or a double bond, and where each heterocycle preferably carries only two substituents of the definition $R^7$ and/or $R^8$ in any desired combination.

Q represents oxygen or sulphur, $R^7$ represents hydrogen, hydroxyl, mercapto, cyano, fluorine, chlorine, bromine, iodine, represents in each case optionally fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, represents methylamino, ethylamino, n- or i-propylamino, n-, i-, s- or t-butylamino, dimethylamino, diethylamino, di-n-propylamino or di-i-propylamino, represents in each case optionally fluorine- and/or chlorine-substituted ethenyl, propenyl, butenyl, ethinyl, propinyl, butinyl, propenyloxy, butenyloxy, propenylthio, butenylthio, propenylamino or butenylamino, represents in each case optionally fluorine and/or chlorine-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or represents in each case optionally fluorine-, chlorine-, methyl-, ethyl-, n- or i-propyl-, n-, i-, s- or t-butyl-, methoxy-, ethoxy-, n- or i-propoxy-substituted phenyl-, phenyloxy-, phenylthio-, phenylamino-, benzyl-, benzyloxy-, benzylthio- or benzylamino- and $R^8$ represents hydrogen, hydroxyl, amino, represents in each case optionally fluorine and/or chlorine-, methoxy- or ethoxy-substituted methyl, ethyl, n- or i-propyl, n-, i- or s-butyl, methoxy, ethoxy, n- or i-propoxy, methylamino, ethylamino or dimethylamino, represents in each case optionally fluorine- and/or chlorine-substituted ethenyl, propenyl, ethinyl, propinyl or propenyloxy, represents in each case optionally fluorine- and/or chlorine-substituted cyclopropyl, cyclobutyl, cyclopentyl, cyclohexyl, cyclopropylmethyl, cyclobutylmethyl, cyclopentylmethyl or cyclohexylmethyl, or represents in each case optionally fluorine-, chlorine- methyl-, ethyl-, n- or i-propyl-, n-, i-, s- or t-butyl-, methoxy-, ethoxy-, n- or i-propoxy-substituted phenyl or benzyl.

$R^1$ very particularly preferably represents hydrogen, amino or methyl.

$R^2$ very particularly preferably represents cyano, carboxyl, carbamoyl, thiocarbamoyl, represents in each case optionally fluorine- and/or chlorine-substituted methyl or ethyl, or represents methoxycarbonyl or ethoxycarbonyl.

$R^3$ very particularly preferably represents hydrogen, fluorine, chlorine, bromine or represents optionally fluorine- and/or chlorine-substituted methyl.

$R^4$ very particularly preferably represents hydrogen, fluorine or chlorine, $R^5$ very particularly preferably represents cyano, thiocarbamoyl, chlorine, bromine or represents in each case optionally fluorine- and/or chlorine-substituted methyl or methoxy.

$R^6$ very particularly preferably represents an optionally nitro-, hydroxyl-, mercapto-, amino-, cyano-, carboxyl-, carbamoyl-, fluorine-, chlorine-, bromine-, iodine-, methyl-, ethyl-, n- or i-propyl, n-, i-, s- or t-butyl-, cyanomethyl, cyanoethyl, cyano-n-propyl, cyano-i-propyl-, carboxymethyl-, carboxyethyl-, carboxy-n-propyl-, carboxy-i-propyl-, fluoromethyl, chloromethyl-, bromomethyl-, difluoromethyl-, dichloromethyl-, trifluoromethyl-, trichloromethyl-, fluorodichloromethyl-, chlorodifluoromethyl-, fluoroethyl-, chloroethyl-, difluoroethyl-, dichloroethyl-, chlorofluoroethyl-, trifluoroethyl-, trichloroethyl-, fluorodichloroethyl-, chlorodifluoroethyl-, tetrafluoroethyl-, chlorotrifluoroethyl-, dichlorodifluoroethyl-, pentafluoroethyl-, methoxymethyl-, ethoxymethyl-, n- or i-propoxymethyl-, methoxyethyl-, ethoxyethyl-, n- or i-propoxyethyl-, methoxypropyl-, ethoxypropyl-, methoxycarbonylmethyl-, ethoxycarbonylmethyl-, n- or i-propoxycarbonylmethyl-, methoxycarbonylethyl-, ethoxycarbonylethyl-, n- or i-propoxycarbonylethyl-, methoxycarbonylpropyl-, ethoxycarbonylpropyl-, methylaminocarbonylmethyl-, ethylaminocarbonylmethyl-, n- or i-propylaminocarbonylmethyl-, methylaminocarbonylethyl-, ethylaminocarbonylethyl, n- or i-propylaminocarbonylethyl, dimethylaminocarbonylmethyl-, dimethylaminocarbonylethyl-, methoxy-, ethoxy-, n- or i-propoxy-, cyanomethoxy-, cyanoethoxy-, cyano-n-propoxy-, cyano-i-propoxy, fluoromethoxy-, difluoromethoxy-, trifluoromethoxy-, fluorodichloromethoxy-, chlorodifluoromethoxy-, fluoroethoxy-, chloroethoxy-, difluoroethoxy-, di-chloroethoxy-, chlorofluoroethoxy-, trifluoroethoxy-, trichloroethoxy-, fluorodichloroethoxy-, chlorodifluoroethoxy-, methoxymethoxy-, ethoxymethoxy, n- or i-propoxymethoxy-, methoxyethoxy-, ethoxyethoxy-, n- or i-propoxyethoxy-, carboxymethoxy-, carboxyethoxy-, methoxycarbonylmethoxy-, ethoxycarbonylmethoxy-, n- or i-propoxycarbonylmethoxy-, methoxycarbonylethoxy-, ethoxycarbonylethoxy-, n- or i-propoxycarbonylethoxy-, methylaminocarbonylmethoxy-, ethylaminocarbonylmethoxy-, n- or i-propylaminocarbonylmethoxy-, methylaminocarbonylethoxy-, ethylaminocarbonylethoxy-, n- or i-propylaminocarbonylethoxy-, dimethylaminocarbonylmethoxy-, dimethylaminocarbonylethoxy-, methoxycarbonyl-, ethoxycarbonyl-, n- or i-propoxycarbonyl-, propenyloxy-, butenyloxy-, propinyloxy-, butinyloxy-, methylthio-, ethylthio-, n- or i-propylthio-, difluoromethylthio-, trifluoromethylthio-, fluorodichloromethylthio-, chlorodifluoromethylthio-, methylsulphinyl-, ethylsulphinyl-, n- or i-propylsulphinyl-, trifluoromethylsulphinyl-, methylsulphonyl-, ethylsulphonyl-, n- or i-propylsulphonyl-, trifluoromethylsulphonyl-, (in each case optionally fluorine, chlorine, methoxy- or ethoxy-substituted)acetylamino-, propionylamino-, nor i-butyroylamino-, methoxycarbonylamino-, ethoxycarbonylamino-, n- or i-propoxycarbonylamino-, (in each case optionally fluorine- and/or chlorine-substituted) methylsulphonylamino-, ethylsulphonylamino-, n- or i-propylsulphonylamino-, (in each case optionally fluorine- and/or chlorine-substituted) cyclopropyl-, cyclobutyl-, cyclopentyl-, cyclohexyl-, cyclopropyloxy-, cyclobutyloxy-, cyclopentyloxy-, cyclohexyloxy-, cyclopropylthio-, cyclobutylthio-, cyclopentylthio-, cyclohexylthio-, cyclopropylamino-, cyclobutylamino-, cyclopentylamino-, cyclohexylamino-, cyclopropylmethyl-, cyclobutylmethyl-, cyclopentylmethyl-, cyclohexylmethyl-, cyclopropylmethoxy-, cyclobutylmethoxy-, cyclopentylmethoxy-, cyclohexylmethoxy-, cyclopropylmethylthio-, cyclobutylmethylthio-, cyclopentylmethylthio-, cyclohexylmethylthio-, cyclopropylmethylamino-, cyclobutylmethylamino-, cyclopentylmethylamino-, cyclohexylmethylamino-, (in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted) phenyl-, pyridyl-, phenyloxy-, phenylthio-, phenylamino-, benzyl-, benzyloxy-, benzylthio- or benzylamino-substituted saturated or unsaturated monocyclic or bicyclic nitrogen-containing heterocyclic grouping, attached via N, from the group consisting of pyrrolyl, pyrrolidinyl, pyrazolyl, imidazolyl, isoxazolidinyl, triazolyl, piperidinyl, morpholinyl, thiomorpholinyl, piperazinyl.

or represents one of the groupings below.

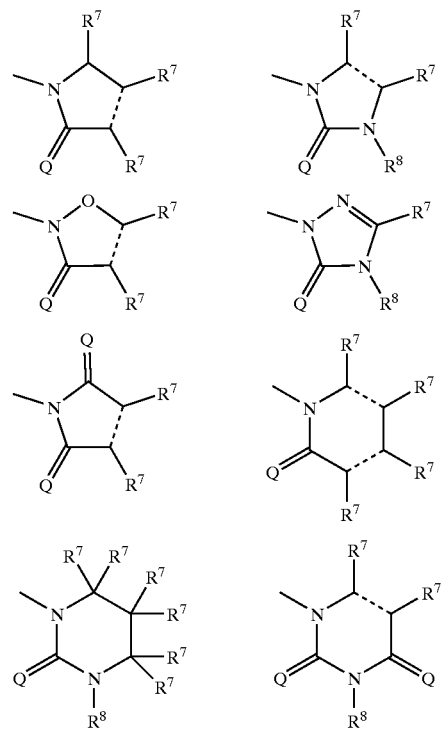

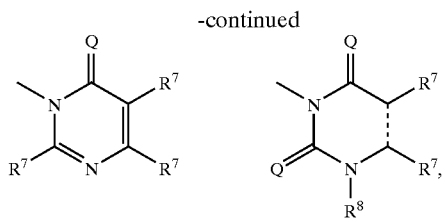

where each of the bonds, shown with a dashed line, is a single bond or a double bond, and where each heterocycle preferably carries only two substitutents of the definition $R^7$ and/or $R^8$ in any desired combination, Q preferably represents oxygen.

$R^7$ preferably represents hydrogen, hydroxyl, mercapto, cyano, fluorine, chlorine, represents in each case optionally fluorine-, chlorine-, methoxy-, ethoxy-, methylthio- or ethylthio-substituted methyl or ethyl, methoxy, ethoxy or methylthio, represents methylamino, ethylamino, dimethylamino or diethylamino, represents in each case optionally fluorine- and/or chlorine-substituted cyclopropyl, cyclobutyl, cyclopentyl, cyclohexyl, cyclopropyloxy, cyclobutyloxy, cyclopentyloxy or cyclohexyloxy, or represents in each case optionally fluorine-, chlorine-, methyl-, ethyl-, methoxy- or ethoxy-substituted phenyl, phenyloxy, benzyl or benzyloxy.

$R^8$ preferably represents hydrogen, hydroxyl, amino, represents in each case optionally fluorine and/or chlorine-methoxy- or ethoxy-substituted methyl or ethyl, methoxy, ethoxy, methylamino, ethylamino or dimethylamino, represents in each case optionally fluorine- and/or chlorine-substituted cyclopropyl, cyclobutyl, cyclopentyl, cyclohexyl, cyclopropylmethyl, cyclobutylmethyl, cyclopentylmethyl or cyclohexylmethyl, or represents in each case optionally fluorine-, chlorinemethyl-, ethyl-, methoxy- or ethoxy-substituted phenyl or benzyl.

$R^2$ most preferably represents in each case fluorine- and/or chlorine-substituted methyl, ethyl, or represents methoxycarbonyl or ethoxycarbonyl.

$R^3$ most preferably represents hydrogen, fluorine, chlorine or represents optionally fluorine- and/or chlorine-substituted methyl.

$R^5$ most preferably represents cyano, chlorine or bromine.

$R^6$ most preferably represents an optionally hydroxyl-, amino-, fluorine-, chlorine-, methyl-, ethyl-, trifluoromethyl-, methylthio-, ethylthio-, methylamino-, dimethylamino-, diethylamino-, cyclopropyl-, cyclobutyl-, cyclopentyl- or cyclohexyl-substituted heterocyclic grouping, attached via N, from the group consisting of pyrrolidinyl, isoxazolidinyl, piperidinyl, morpholinyl, thiomorpholinyl, piperazinyl or represents one of the groupings below

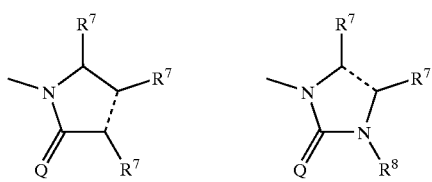

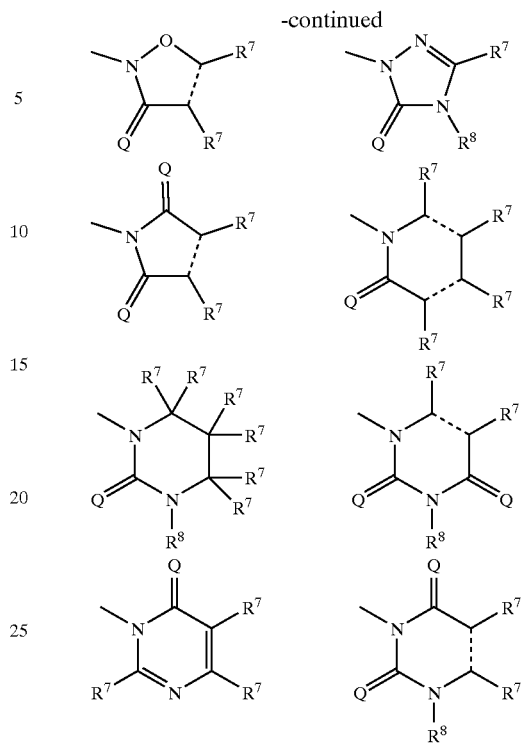

$R^6$ specially preferably represents the grouping

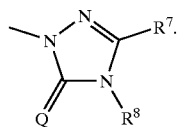

The invention preferably also provides sodium, potassium, magnesium, calcium, ammonium, $C_1$–$C_4$-alkyl-ammonium-, di-($C_1$–$C_4$-alkyl)-ammonium-, tri-($C_1$–$C_4$-alkyl)-ammonium-, tetra-($C_1$–$C_4$-alkyl)-ammonium, tri-($C_1$–$C_4$-alkyl)-sulphonium-, $C_5$- or $C_6$-cycloalkyl-ammonium- and di-($C_1$–$C_2$-alkyl)-benzyl-ammonium salts of compounds of the formula (I) in which $A^1$, $A^2$, $R^1$, $R^2$, $R^3$, $R^4$, $R^5$ and $R^6$ are each as defined above, or else complex compounds (co-ordination compounds) of these compounds with metals such as copper, iron, cobalt, nickel.

Preference according to the invention is given to those compounds of the formula (I) which contain a combination of the meanings listed above as being preferred.

Particular preference according to the invention is given to those compounds of the formula (I) which contain a combination of the meanings listed above as being particularly preferred.

Very particular preference according to the invention is given to those compounds of the formula (I) which contain a combination of the meanings listed above as being very particularly preferred.

More preference according to the invention is given to those compounds of the formula (I) which contain a combination of the meanings listed above as being most preferred.

The general or preferred radical definitions listed above apply both to the end products of the formula (I) and, correspondingly, to the starting materials or intermediates required in each case for the preparation. These radical definitions can be combined with one another as desired, i.e. including combinations between the given preferred ranges.

A very particularly preferred group are those compounds of the formula (I) in which $R^1$ represents hydrogen, amino or methyl, $R^2$ represents cyano or trifluoromethyl, $R^3$ represents hydrogen, fluorine, chlorine or methyl, $R^4$ represents hydrogen, fluorine or chlorine, $R^5$ represents cyano, thiocarbamoyl, chlorine or bromine, $R^6$ represents the grouping below,

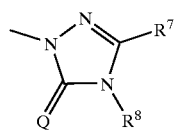

Q represents oxygen, $R^7$ represents hydrogen, chlorine, bromine, iodine, represents in each case optionally fluorine-, chlorine-, methoxy-, ethoxy-, methylthio-, ethylthio-, methylsulphinyl-, ethylsulphinyl-, methylsulphonyl- or ethylsulphonyl-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, represents methylamino, ethylamino, n- or i-propylamino, dimethylamino or diethylamino, represents in each case optionally fluorine- and/or chlorine-substituted ethenyl, propenyl, ethinyl, propinyl, propenyloxy, propenylthio or propenylamino, represents optionally fluorine- and/or chlorine-substituted cyclopropyl, or represents in each case optionally fluorine-, chlorine-, methyl-, ethyl-, methoxy- or ethoxy-substituted phenyl, phenyloxy, phenylthio, phenylamino, benzyl, benzyloxy, benzylthio or benzylamino, and $R^8$ represents hydrogen, amino, represents in each case optionally fluorine- and/or chlorine- methoxy- or ethoxy-substituted methyl, ethyl, n- or i-propyl, methoxy, ethoxy, n- or i-propoxy, represents optionally fluorine- and/or chlorine-substituted cyclopropyl, or represents in each case optionally fluorine- or chlorine-, methyl-, ethyl-, methoxy- or ethoxy-substituted phenyl or benzyl.

The novel substituted phenyl uracils of the general formula (I) have interesting biological properties. In particular, they have strong herbicidal activity.

The novel substituted phenyl uracils of the general formula (I) are obtained when halogenomethyl-phenyl uracils of the general formula (II)

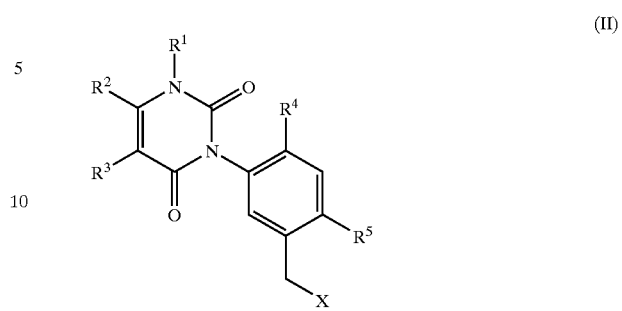

in which $R^1$, $R^2$, $R^3$, $R^4$ and $R^5$ are each as defined above and

X represents halogen, are reacted with nitrogen heterocycles of the general formula (III)

$$H—R^6 \quad (III)$$

in which $R^6$ is as defined above, if appropriate in the presence of one or more reaction auxiliaries and if appropriate in the presence of one or more diluents, and, if appropriate, the resulting compounds of the general formula (I) are subsequently converted in a customary manner—in general by electrophilic or nucleophilic substitution reactions or oxidation or reduction reactions or additional reactions—into other compounds of the general formula (I) within the scope of the definition of the substituents.

The compounds of the general formula (I) can be converted by customary methods into other compounds of the general formula (I) according to the above definition, for example by amination or alkylation (for example $R^1$: H→$NH_2$, H→$CH_3$), reaction with dicyanogen or hydrogen sulphide (for example $R^5$: Br→CN, CN→$CSNH_2$, cf. the Preparation Examples).

Using, for example, 2-bromomethyl-5-fluoro-4-(3-methyl-2,6-dioxo-4-trifluoromethyl-3,6-dihydro-1(2H)-pyrimidinyl)-benzonitrile and morpholine as starting materials, the course of the reaction in the process according to the invention can be illustrated by the following equation:

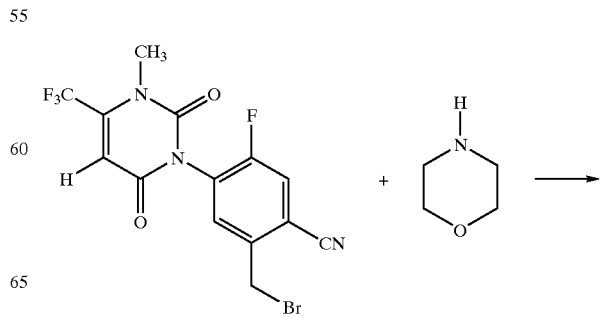

-continued

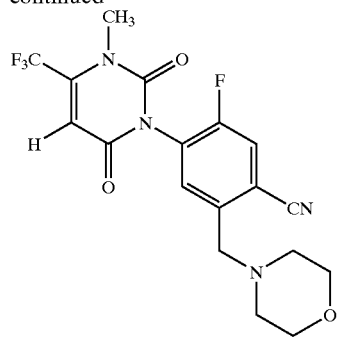

The formula (II) provides a general definition of the halogenomethyl-phenyl uracils to be used as starting materials in the process according to the invention for preparing compounds of the general formula (I). In the general formula (II), $R^1$, $R^2$, $R^3$, $R^4$ and $R^5$ each preferably or in particular have those meanings which have already been mentioned above, in connection with the description of the compounds of the general formula (I) according to the invention, as being preferred, particularly preferred, very particularly preferred or most preferred for $R^1$, $R^2$, $R^3$, $R^4$, $R^5$ and $R^6$; X preferably represents fluorine, chlorine, bromine or iodine, in particular chlorine or bromine.

The starting materials of the general formula (II) have hitherto not been disclosed in the literature; as novel substances, they also form part of the subject-matter of the present application.

The novel halogenomethyl-phenyl uracils of the general formula (II) are obtained when methylphenyl uracils of the general formula (IV)

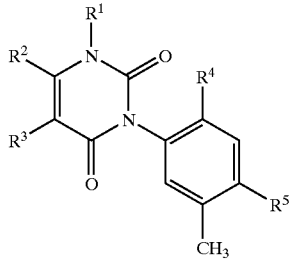

in which
$R^1$, $R^2$, $R^3$, $R^4$ and $R^5$ are each as defined above,
are reacted with halogenating agents, such as, for example, N-bromo-succinimide or N-chloro-succinimide, in the presence of reaction auxiliaries, such as, for example, 2,2'-azo-bis-(2-methyl-propionitrile) alias 2,2'-azoisobutyronitrile, and in the presence of diluents, such as, for example, carbon tetrachloride, at temperatures between 50° C. and 100° C. (cf. the Preparation Examples).

The methylphenyl uracils of the general formula (IV) required as precursors have hitherto not been disclosed in the literature; as novel substances, they also form part of the subject-matter of the present application.

The novel methylphenyl uracils of the general formula (IV) obtained when aminoalkenoic esters of the general formula (V)

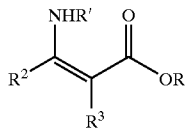

in which
$R^1$, $R^2$ and $R^3$ are each as defined above and
R represents alkyl, aryl or arylalkyl (preferably $C_1$–$C_4$-alkyl, phenyl or benzyl, in particular methyl or ethyl)
are reacted with methylphenyl isocyanates of the general formula (VI)

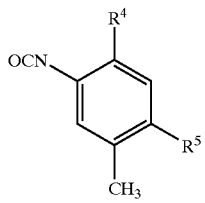

in which
$R^4$ and $R^5$ are each as defined above or with methylphenyl urethanes (methylphenyl carbamates) of the general formula (VII)

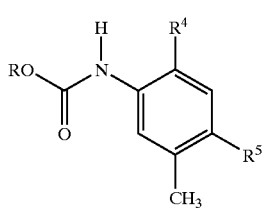

in which
$R^4$ and $R^5$ are each as defined above and
R represents alkyl, aryl or arylalkyl (preferably $C_1$–$C_4$-alkyl, phenyl or benzyl, in particular methyl or ethyl),
if appropriate in the presence of a reaction auxiliary, such as, for example, sodium hydride, and if appropriate in the presence of a diluent, such as, for example, N,N-dimethyl-formamide at temperatures between 0° C. and 150° C.,
and, if appropriate, the resulting compounds of the general formula (IV) are subsequently converted in a customary manner—in general by electrophilic or nucleophilic substitution reactions—into other compounds of the general formula (IV) within the scope of the definition of the substituents.

The compounds of the general formula (IV) can be converted by customary methods into other compounds of the general formula (IV) according to the above definition, for example by amination or alkylation (for example $R^1$: H→$NH_2$, H→$CH_3$), reaction with dicyanogen or hydrogen sulphide (for example $R^5$: Br→CN, CN→$CSNH_2$, cf. the Preparation Examples).

The amino alkenoic esters of the general formula (V) required as precursors are known and/or can be prepared by processes known per se (cf. J. Heterocycl. Chem. 9 (1972), 513–522).

Except for the compound 3-methyl-4-bromo-phenyl isocyanate (cf. GB-A-1503244) and the compound O-methyl and O-ethyl N-(4-bromo-3-methyl-phenyl)-carbamate) cf. WO-A-96/19477), the methylphenyl isocyanates of the general formula (VI) and the methylphenyl urethanes of the general formula (VII) furthermore required as precursors have hitherto not been disclosed in the literature, and with the exception of the compounds specifically mentioned above (4-bromo-3-methyl-phenylisocyanate, O-methyl and O-ethyl N-(4-bromo-3-methyl-phenyl)-carbamate) may also form, as novel substances, part of the subject-matter of the present application. Particularly preferred here are the novel compounds 4-bromo-2-fluoro-5-methylphenylisocyanate and 4-cyano-2-fluoro-5-methyl-phenylisocyanate and O-methyl and O-ethyl N-(4-bromo-2-fluoro-5-methyl-phenyl)-carbamate and O-methyl and O-ethyl N-(4-cyano-2-fluoro-5-methyl-phenyl)-carbamate.

Methylphenyl isocyanates of the general formula (VI) are obtained when toluidine derivatives of the general formula (VIII)

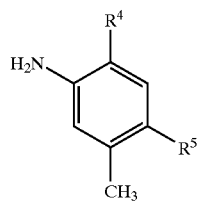

(VIII)

in which
$R^4$ and $R^5$ are each as defined above,
are reacted with phosgene in the presence of a diluent, such as, for example, chlorobenzene, at temperatures between −20° C. and +150° C. (cf. also EP-A-648749).

The methylphenyl urethanes of the general formula (VII) are obtained when toluidine derivatives of the general formula (VIII)

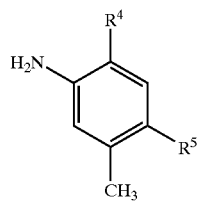

(VIII)

in which
$R^4$ and $R^5$ are each as defined above,
are reacted with chlorocarbonyl compounds of the general formula (IX)

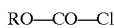 (IX)

in which
R is as defined above,
if appropriate in the presence of an acid acceptor such as, for example, pyridine, and if appropriate in the presence of a diluent, such as, for example, methylene chloride, at temperatures between −20° C. and +100° C. (cf. the Preparation Examples).

Except for the compounds 4-amino-2-methyl-benzonitrile (cf. U.S. Pat. No. 4,191,775) and 4-bromo-3-methyl-aniline (cf. WO-A-98/50358), the toluidine derivatives of the general formula (VIII) required as precursors have hitherto not been disclosed in the literature, and with the exception of the compounds 4-amino-2-methyl-benzonitrile and 4-bromo-3-methyl-aniline they also form, as novel substances, part of the subject-matter of the present application. Particular preference is given here to the novel compounds 4-bromo-2-fluoro-5-methyl-aniline and 4-cyano-2-fluoro-5-methyl-aniline (alias 4-amino-5-fluoro-2-methyl-benzonitrile).

The toluidine derivatives of the general formula (VIII) are obtained when toluidines of the general formula (X)

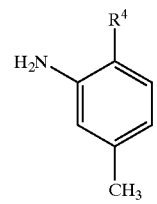

(X)

in which
$R^4$ is as defined above,
are reacted with a brominating agent, such as, for example, benzyl-trimethylammonium tribromide, if appropriate in the presence of a reaction auxiliary, such as, for example, calcium carbonate, if appropriate in the presence of one or more diluents, such as, for example, dichloromethane and methanol, at temperatures between 0° C. and 100° C. (cf. the Preparation Examples), and the resulting 4-bromo-3-methyl-aniline derivatives are, if appropriate, reacted with a cyanating agent, such as, for example, copper (I) cyanide, if appropriate in the presence of a diluent, such as, for example, N,N-dimethyl-formamide, at temperatures between 120° C. and 180° C.

The formula (III) provides a general definition of the nitrogen heterocycles further to be used as starting materials in the process according to the invention for preparing compounds of the general formula (I). In the general formula (III), $R^6$ preferably has the meaning which has already been mentioned above, in connection with the description of the compounds of the general formula (I) according to the invention, as being preferred, particularly preferred, very particularly preferred or most preferred for $R^6$.

The compounds of the formulae (IX) and (X) are known organic chemicals. In the general formula (X), $R^4$ preferably has that meaning which has already been mentioned above, in connection with the description of the compounds of the general formula (I) according to the invention, as being preferred, particularly preferred or very particularly preferred for $R^4$.

The starting materials of the general formula (III) are known organic chemicals.

The process according to the invention for preparing the compounds of the general formula (I) is preferably carried out using one or more reaction auxiliaries. Suitable reaction auxiliaries for the process according to the invention are generally the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide, furthermore also basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methylpyridine, 4-dimethylaminopyridine, N-methyl-piperidine, 1,4-diazabicyclo[2.2.2]-octane (DABCO), 1,5-diazabicyclo[4.3.0]-non-5-ene (DBN), or 1,8-diazabicyclo[5.4.0]-undec-7-ene (DBU).

Further reaction auxiliaries suitable for the process according to the invention are phase-transfer catalysts. Examples of such catalysts which may be mentioned are:

Tetrabutylammonium bromide, tetrabutylammonium chloride, tetraoctylammonium chloride, tetrabutylammonium hydrogen sulphate, methyl-trioctylammonium chloride, hexadecyl-trimethylammonium chloride, hexadecyl-trimethylammonium bromide, benzyl-trimethylammonium chloride, benzyl-triethylammonium chloride, benzyl-trimethylammonium hydroxide, benzyl-triethylammonium hydroxide, benzyl-tributylammonium chloride, benzyl-tributylammonium bromide, tetrabutyl-phosphonium bromide, tetrabutylphosphonium chloride, tributyl-hexadecylphosphonium bromide, butyl-triphenylphosphonium chloride, ethyl-trioctylphosphonium bromide, tetraphenylphosphonium bromide.

The process according to the invention for preparing the compounds of the general formula (I) is preferably carried out using one or ore diluents. Suitable diluents for carrying out the process according to the invention are, in addition to water, especially inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride, ethers, such as diethyl ether, diisopropylether, dioxane, tetrahydrofuran or ethylene glycol dimethyl ether or ethylene glycol diethylether; ketones, such as acetone, butanone or methyl isobutyl ketones; nitriles, such as acetonitrile, propionitrile or butyronitrile, amides such as N,N-dimethylformamide, N,N-dimethylacetamide, N-methyl-formanilide, N-methyl-pyrrolidone or hexamethylphosphoric triamide; esters, such as methyl acetate or ethyl acetate, sulphoxides, such as dimethylsulphoxide, alcohols, such as methanol, ethanol, n- or i-propanol, ethylene glycol monomethyl ether, ethylene glycol monoethyl ether, diethylene glycol monomethyl ether, diethyleneglycol-monoethyl ether, mixtures thereof with water or pure water.

When carrying out the process according to the invention, the reaction temperatures can be varied within a relatively wide range. In general, the process is carried out at temperatures between 0° C. and 150° C., preferably between 10° C. and 120° C.

The process according to the invention is generally carried out under atmospheric pressure. However, it is also possible to carry out the process according to the invention under elevated or reduced pressure—in general between 0.1 bar and 10 bar.

For carrying out the process according to the invention, the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred at the required temperature for several hours. Work-up is carried out by customary methods (cf. the Preparation Examples).

The active compounds according to the invention can be used as defoliants, desiccants, haulm killers and, especially, as weed killers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad active spectrum when used on the soil and on above-ground parts of plants. To a certain extent they are also suitable for the selective control of monocotyledonous and dicotyledonous weeds in monocotyledonous and dicotyledonous crops, both by the pre-emergence and by the post-emergence method. At certain concentrations or application rates, the active compounds according to the invention can also be employed for controlling animal pests and fungal or bacterial plant diseases. If appropriate, they can also be used as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are: for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, beflubutamid, benazolin (-ethyl), benfuresate, bensulfuron (-methyl), bentazon, benzfendizone, benzobicyclon, benzofenap, benzoylprop(-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (—P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (—P-ethyl), fentrazamide, flamprop (-isopropyl, -isopropyl-L, -methyl), flazasulfuron, florasulam, fluazifop (—P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, —P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinrmerac, quinoclamine, quizalofop(—P-ethyl, —P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

Furthermore suitable for the mixtures are known softeners, for example AD-67, BAS-145138, benoxacor, cloquintocet (-mexyl), cyometrinil, 2,4-D, DKA-24, dichlormid, dymron, fenclorim, fenchlorazol (-ethyl), flurazole, fluxofenim, furilazole, isoxadifen (-ethyl), MCPA, mecoprop (—P), mefenpyr (-diethyl), MG-191, oxabetrinil, PPG-1292, R-29148.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetical engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having certain properties ("traits") and which have been obtained by conventional breeding, by mutagenesis or by recombinant DNA techniques. They can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention—also in combination with other agro-chemical active compounds—, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetical engineering) which are preferably treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasised examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasised are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased defence of the plants to fungi, bacteria and viruses by systemic acquired resistance (SAR), systemin, phytoalexins, elicitors and resistance genes and correspondingly expressed proteins and toxins. Traits that are furthermore particularly emphasised are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylurea, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the general formula (I) or the active compound mixtures according to the invention where in addition to the good control of weed plants, the abovementioned synergistic effects with the transgenic plants of plant cultivars occur. The preferred ranges stated above for the active compounds or mixtures also apply to the treatment of these plants. Particular emphasis is given to the treatment of plants with the compounds or mixtures specifically mentioned in the present text.

The following examples show the preparation and use of the active compounds according to the invention:

PREPARATION EXAMPLES

Example 1

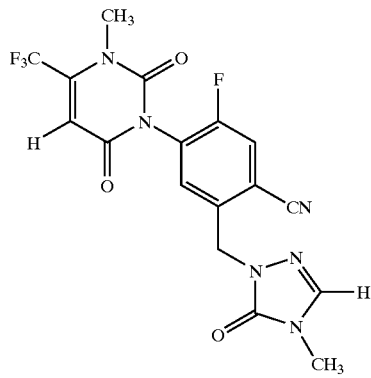

A mixture of 1.20 g (1.63 mMol) of 2-bromomethyl-5-fluoro-4-(3-methyl-2,6-dioxo-4-trifluoromethyl-3,6-dihydro-1(2H)-pyrimidinyl)-benzonitrile, 0.15 g (1.54 mMol) of 4-methyl-2,4-dihydro-3H-1,2,4-triazol-3-one, 0.45 g (3.25 mMol) of potassium carbonate and 50 ml of acetonitrile is heated to the boil at reflux for 18 hours. The mixture is subsequently concentrated under reduced pressure using a rotary evaporator and the residue is taken up in 1 N hydrochloric acid and extracted with ethyl acetate. The organic phase is dried with sodium sulphate and filtered. The filtrate is concentrated under reduced pressure and the residue is purified by column chromatography- silica gel, 1.fraction using methylene chloride, 2.fraction using ethyl acetate, 3.fraction using methanol- and the product is isolated from the 3.fraction by concentration.

This gives 0.32 g (46% of theory) of 5-fluoro-4-(3-methyl-2,6-dioxo-4-trifluoromethyl-3,6-dihydro-1(2H)-pyrimidinyl)-2-[(4-methyl-5-oxo-4,5-dihydro-1H-1,2,4-triazol-1-yl)-methyl]-benzonitrile.

$^1$H-NMR (DMSO-D$_6$, δ): 6.57 ppm.

Similarly to Example 1, and in accordance with the general description of the preparation process according to the invention, it is also possible to prepare, for example, the compounds of the general formula (I) listed in Table 1 below.

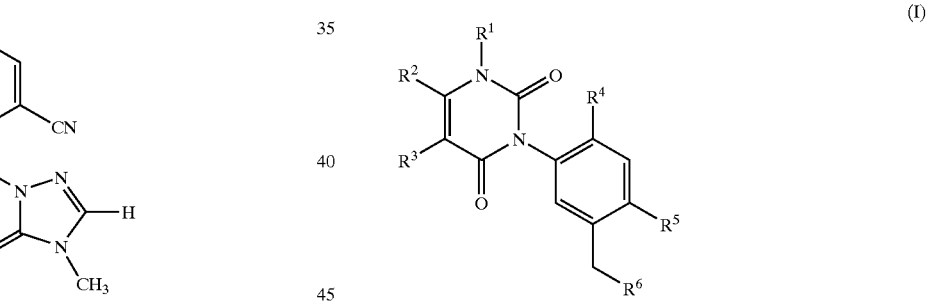

TABLE 1

Examples of compounds of the formula (I)

| Exp. No. | R$^1$ | R$^2$ | R$^3$ | R$^4$ | R$^5$ | R$^6$ | Physical data |
|---|---|---|---|---|---|---|---|
| 2 | CH$_3$ | CF$_3$ | H | H | Br | ![triazolone with CH3, CH3] | $^1$H-NMR (DMSO-D$_6$, δ): 4.89 ppm |
| 3 | CH$_3$ | CF$_3$ | H | F | Br | ![triazolone with CH3, CH3] | $^1$H-NMR (DMSO-D$_6$, δ): 4.88 ppm |

TABLE 1-continued

Examples of compounds of the formula (I)

| Exp. No. | R¹ | R² | R³ | R⁴ | R⁵ | R⁶ | Physical data |
|---|---|---|---|---|---|---|---|
| 4 | $CH_3$ | $CF_3$ | H | F | CN | 2,4-dimethyl-5-methyl-2,4-dihydro-3H-1,2,4-triazol-3-one | $^1$H-NMR (DMSO-D$_6$, δ): 5.02 ppm |
| 5 | $CH_3$ | $CF_3$ | H | F | Br | 2,4-dimethyl-5-methylthio-2,4-dihydro-3H-1,2,4-triazol-3-one | m.p.: 153° C. |
| 6 | $CH_3$ | $CF_3$ | H | F | Br | 2,4-dimethyl-5-methoxy-2,4-dihydro-3H-1,2,4-triazol-3-one | m.p.: 181° C. |
| 7 | $CH_3$ | $CF_3$ | H | F | Br | 2,4-dimethyl-5-dimethylamino-2,4-dihydro-3H-1,2,4-triazol-3-one | logP = 2.33$^{a)}$ |
| 8 | $CH_3$ | $CF_3$ | H | F | Br | 5-bromo-2,4-dimethyl-2,4-dihydro-3H-1,2,4-triazol-3-one | logP = 2.50$^{a)}$ |
| 9 | $CH_3$ | $CF_3$ | H | F | Br | 1-methyl-6-trifluoromethyl-pyrimidin-2(1H)-one | logP = 2.98$^{a)}$ |
| 10 | $CH_3$ | $CF_3$ | H | F | Br | 1-methyl-5-trifluoromethyl-uracil | logP = 2.61$^{a)}$ |
| 11 | $CH_3$ | $CF_3$ | H | F | CN | 2,4-dimethyl-5-methyl-2,4-dihydro-3H-1,2,4-triazol-3-one | logP = 1.55$^{a)}$ |
| 12 | $CH_3$ | $CF_3$ | H | F | CN | 2,4-dimethyl-5-dimethylamino-2,4-dihydro-3H-1,2,4-triazol-3-one | $^1$H-NMR (DMSO-D$_6$, δ): 5.00 ppm |
| 13 | $CH_3$ | $CF_3$ | H | F | CN | 2,4-dimethyl-5-methylthio-2,4-dihydro-3H-1,2,4-triazol-3-one | logP = 2.25$^{a)}$ |

TABLE 1-continued

Examples of compounds of the formula (I)

| Exp. No. | R¹ | R² | R³ | R⁴ | R⁵ | R⁶ | Physical data |
|---|---|---|---|---|---|---|---|
| 14 | CH₃ | CF₃ | H | F | CN | 1,4-dimethyl-3-bromo-1,2,4-triazol-5(4H)-one-2-yl | |
| 15 | CH₃ | CF₃ | H | F | CN | 1,4-dimethyl-3-methoxy-1,2,4-triazol-5(4H)-one-2-yl | logP = 1.94[a] |
| 16 | CH₃ | CF₃ | H | F | Cl | 1,4-dimethyl-3-methyl-1,2,4-triazol-5(4H)-one-2-yl | logP = 1.99[a] |
| 17 | CH₃ | CF₃ | H | F | Cl | 1,4-dimethyl-3-methoxy-1,2,4-triazol-5(4H)-one-2-yl | logP = 2.23[a] |
| 18 | CH₃ | CF₃ | H | F | Cl | 1,4-dicyclopropyl-1,2,4-triazol-5(4H)-one-2-yl | logP = 2.69[a] |
| 19 | CH₃ | CF₃ | H | F | Cl | 1,4-dimethyl-3-methylthio-1,2,4-triazol-5(4H)-one-2-yl | logP = 2.49[a] |
| 20 | NH₂ | CF₃ | H | F | Br | 1,4-dimethyl-3-methyl-1,2,4-triazol-5(4H)-one-2-yl | |
| 21 | NH₂ | CF₃ | H | F | CN | 1,4-dimethyl-3-methyl-1,2,4-triazol-5(4H)-one-2-yl | |
| 22 | NH₂ | CF₃ | H | F | Cl | 1,4-dimethyl-3-methyl-1,2,4-triazol-5(4H)-one-2-yl | |
| 23 | NH₂ | CF₃ | H | F | Br | 1,4-dimethyl-3-methylthio-1,2,4-triazol-5(4H)-one-2-yl | |

TABLE 1-continued

Examples of compounds of the formula (I)

| Exp. No. | R¹ | R² | R³ | R⁴ | R⁵ | R⁶ | Physical data |
|---|---|---|---|---|---|---|---|
| 24 | NH₂ | CF₃ | H | F | CN | 1,4-dimethyl-3-(methylthio)-5-oxo-4,5-dihydro-1H-1,2,4-triazol-1-yl | |
| 25 | NH₂ | CF₃ | H | F | Cl | 1,4-dimethyl-3-(methylthio)-5-oxo-4,5-dihydro-1H-1,2,4-triazol-1-yl | |
| 26 | NH₂ | CF₃ | H | F | Br | 3-methoxy-1,4-dimethyl-5-oxo-4,5-dihydro-1H-1,2,4-triazol-1-yl | |
| 27 | NH₂ | CF₃ | H | F | CN | 3-methoxy-1,4-dimethyl-5-oxo-4,5-dihydro-1H-1,2,4-triazol-1-yl | |
| 28 | NH₂ | CF₃ | H | F | Cl | 3-methoxy-1,4-dimethyl-5-oxo-4,5-dihydro-1H-1,2,4-triazol-1-yl | |
| 29 | NH₂ | CF₃ | H | F | Br | 3-(dimethylamino)-1,4-dimethyl-5-oxo-4,5-dihydro-1H-1,2,4-triazol-1-yl | |
| 30 | NH₂ | CF₃ | H | F | CN | 3-(dimethylamino)-1,4-dimethyl-5-oxo-4,5-dihydro-1H-1,2,4-triazol-1-yl | |
| 31 | NH₂ | CF₃ | H | F | Cl | 3-(dimethylamino)-1,4-dimethyl-5-oxo-4,5-dihydro-1H-1,2,4-triazol-1-yl | |
| 32 | CH₃ | CF₃ | H | F | Br | 1,3-dimethyl-2-oxoimidazolidin-1-yl | |
| 33 | CH₃ | CF₃ | H | F | CN | 1,3-dimethyl-2-oxoimidazolidin-1-yl | |

TABLE 1-continued

Examples of compounds of the formula (I)

| Exp. No. | R¹ | R² | R³ | R⁴ | R⁵ | R⁶ | Physical data |
|---|---|---|---|---|---|---|---|
| 34 | CH₃ | CF₃ | H | F | Cl | 1,3-dimethyl-imidazolidin-2-one | |
| 35 | CH₃ | CF₃ | H | F | Br | 1,3-dimethyl-tetrahydropyrimidin-2-one | |
| 36 | CH₃ | CF₃ | H | F | CN | 1,3-dimethyl-tetrahydropyrimidin-2-one | |
| 37 | CH₃ | CF₃ | H | F | Cl | 1,3-dimethyl-tetrahydropyrimidin-2-one | |
| 38 | CH₃ | CF₃ | H | F | Br | 1-methyl-pyrrolidin-2-one | |
| 39 | CH₃ | CF₃ | H | F | CN | 1-methyl-pyrrolidin-2-one | |
| 40 | CH₃ | CF₃ | H | F | Cl | 1-methyl-pyrrolidin-2-one | |
| 41 | CH₃ | CF₃ | H | F | Br | 1-methyl-piperidin-2-one | |
| 42 | CH₃ | CF₃ | H | F | CN | 1-methyl-piperidin-2-one | |
| 43 | CH₃ | CF₃ | H | F | Cl | 1-methyl-piperidin-2-one | |

TABLE 1-continued
Examples of compounds of the formula (I)
| Exp. No. | R¹ | R² | R³ | R⁴ | R⁵ | R⁶ | Physical data |
|---|---|---|---|---|---|---|---|
| 44 | CH₃ | CF₃ | H | F | Br |  | |
| 45 | CH₃ | CF₃ | H | F | CN |  | |
| 46 | CH₃ | CF₃ | H | F | Cl |  | |
| 47 | CH₃ | CF₃ | H | F | Br |  | |
| 48 | CH₃ | CF₃ | H | F | CN |  | |
| 49 | CH₃ | CF₃ | H | F | Cl |  | |
| 50 | CH₃ | CF₃ | H | F | Br | 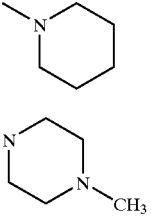 | |
| 51 | CH₃ | CF₃ | H | F | CN | 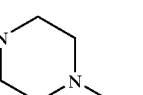 | |
| 52 | CH₃ | CF₃ | H | F | Cl | 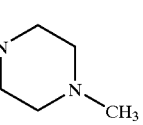 | |
| 53 | CH₃ | CF₃ | H | F | Br |  | |
| 54 | CH₃ | CF₃ | H | F | CN |  | |
| 55 | CH₃ | CF₃ | H | F | Cl |  | |
| 56 | CH₃ | CF₃ | H | F | Br |  | m.p.: 110° C. |
| 57 | CH₃ | CF₃ | H | F | CN |  | |

TABLE 1-continued
Examples of compounds of the formula (I)
| Exp. No. | R¹ | R² | R³ | R⁴ | R⁵ | R⁶ | Physical data |
|---|---|---|---|---|---|---|---|
| 58 | CH₃ | CF₃ | H | F | Cl |  | |
| 59 | CH₃ | CF₃ | H | F | Br | 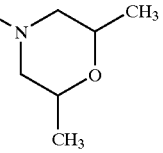 | |
| 60 | CH₃ | CF₃ | H | F | CN | 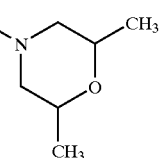 | |
| 61 | CH₃ | CF₃ | H | F | Cl | 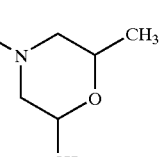 | |
| 62 | CH₃ | CF₃ | H | F | Br | 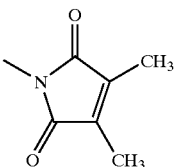 | |
| 63 | CH₃ | CF₃ | H | F | CN | 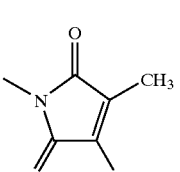 | |
| 64 | CH₃ | CF₃ | H | F | Cl | 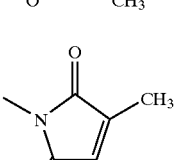 | |
| 65 | CH₃ | CF₃ | H | F | Br |  | |
| 66 | CH₃ | CF₃ | H | F | CN |  | |
| 67 | CH₃ | CF₃ | H | F | Cl |  | |

TABLE 1-continued

Examples of compounds of the formula (I)

| Exp. No. | R¹ | R² | R³ | R⁴ | R⁵ | R⁶ | Physical data |
|---|---|---|---|---|---|---|---|
| 68 | $CH_3$ | $CF_3$ | H | F | Br | 2-methyl-4,4-dimethyl-isoxazolidin-3-one | |
| 69 | $CH_3$ | $CF_3$ | H | F | CN | 2-methyl-4,4-dimethyl-isoxazolidin-3-one | |
| 70 | $CH_3$ | $CF_3$ | H | F | Cl | 2-methyl-4,4-dimethyl-isoxazolidin-3-one | |
| 71 | $CH_3$ | $CF_3$ | H | F | Br | 4-(ethoxycarbonyl)piperazin-1-yl | m.p.: 254° C. |
| 72 | $CH_3$ | $CF_3$ | H | F | Br | 4-[(N,N-dimethylcarbamoyl)methyl]piperazin-1-yl | |
| 73 | $CH_3$ | $CF_3$ | H | F | Br | 4-(pyridin-2-yl)piperazin-1-yl | |
| 74 | $CH_3$ | $CF_3$ | H | F | Br | 2-methyl-pyrrolo[1,2-d][1,2,4]triazin-4(2H)-one | logP = 3.09[a] |
| 75 | $CH_3$ | $CF_3$ | H | F | Br | 1,3-dimethyl-6-trifluoromethyl-pyrimidine-2,4(1H,3H)-dione | logP = 3.18[a] |

The log P values stated in Table 1 were determined in accordance with EEC directive 79/831 Annex V.A8 by HPLC (High Performance Liquid Chromatography) using a reverse-phase column (C 18). Temperature: 43° C.
(a) Mobile phases for the determination in the acidic range: 0.1% aqueous phosphoric acid, acetonitrile; linear gradient from 10% acetonitrile to 90% acetonitrile—the corresponding measurement data in Table 1 are marked a).
(b) Mobile phases for the determination in the neutral range: 0.01 molar aqueous phosphate buffer solution, acetonitrile; linear gradient from 10% acetonitrile to 90% acetonitrile—the corresponding measurement data in Table 1 are labelled b).

Calibration was carried out using unbranched alkane-2-ones (having 3 to 16 carbon atoms) with known log P values (determination of the log P values by the retention times using linear interpolation between two successive alkanols).

The lambda max values were determined in the maxima of the chromatographic signals using the UV spectra from 200 mm to 400 nm.

Starting Materials of the Formula (II):

Example (II-1)

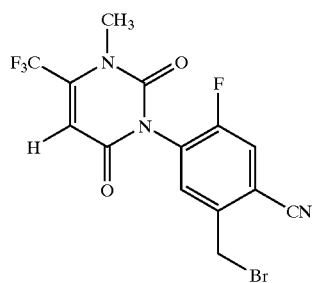

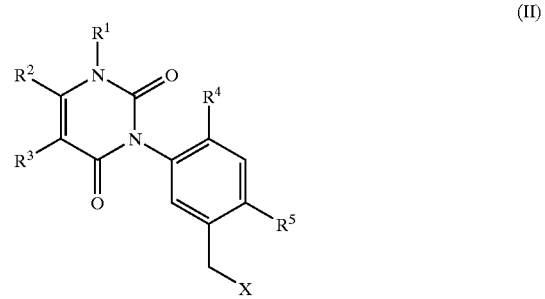

TABLE 2

| | Examples of compounds of the formula (II) | | | | | |
|---|---|---|---|---|---|---|
| Ex. No. | $R^1$ | $R^2$ | $R^3$ | $R^4$ | $R^5$ | X | Physical Data |
| II-2 | $CH_3$ | $CF_3$ | H | F | Br | Br | $^1$H-NMR (DMSO-$D_6$, δ): 4.75 ppm |
| II-3 | $CH_3$ | $CF_3$ | H | F | Br | Cl | |
| II-4 | $CH_3$ | $CF_3$ | H | F | CN | Cl | |
| II-5 | $CH_3$ | $CF_3$ | H | H | CN | Cl | |
| II-6 | $CH_3$ | $CF_3$ | H | Cl | Cl | Cl | |
| II-7 | $CH_3$ | $CF_3$ | H | H | CN | Br | |
| II-8 | $CH_3$ | $CF_3$ | Cl | F | CN | Br | |
| II-9 | $CH_3$ | $CF_3$ | $CH_3$ | F | CN | Br | |

Starting Materials of the Formula (IV):

Example (IV-1)

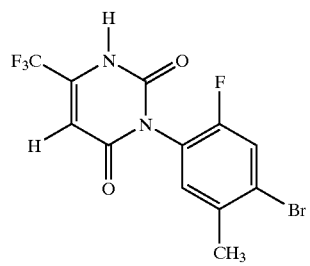

A mixture of 0.80 g (2.44 mMol) of 5-fluoro-2-methyl-4-(3-methyl-2,6-dioxo-4-trifluoromethyl-3,6-dihydro-1 (2H)-pyrimidinyl)-benzonitrile, 0.52 g (2.93 mMol) N-bromosuccinimide, 0.10 g of 2,2'-azodiisobuttyronitrile and 50 ml of carbon tetrachloride is heated to the boil under reflux for 18 hours and, after cooling to room temperature, added from a separating funnel to 5% strength aqueous sodium bicarbonate solution. The aqueous phase is separated off and extracted twice with methylene chloride. The organic phases are combined, dried with sodium sulphate and filtered. From the filtrate, the solvent is carefully distilled off under reduced pressure.

This gives 1.20 g (68% of theory, with a content of 56%) of 2-bromomethyl-5-fluoro-4-(3-methyl-2,6-dioxo-4-trifluoromethyl-3,6-dihydro-1(2H)-pyrimidinyl)benzonitrile.

$^1$H-NMR (DMSO-$D_6$, δ): 4.68 ppm.

Similarly to Example (II-1), it is also possible to prepare, for example, the compounds of the general formula (II) listed in Table 2 below.

At room temperature (about 20° C.), 2.5 g of sodium hydride are added with stirring to a mixture of 14.5 g (78 mMol) of ethyl 3-amino-4,4,4-trifluoro-crotonate and 200 ml N-methyl-pyrrolidone, and the mixture is stirred at room temperature for 15 minutes. 14.3 g (52 mMol) of O-ethyl N-(4-bromo-2-fluoro-5-methyl-phenyl)-carbamate are then added, and the reaction mixture is heated to the boil under reflux for 8 hours and then stirred at room temperature for another 12 hours. The mixture is then poured into 300 ml of a 1N hydrochloric acid, and the resulting crystalline product is isolated by filtration with suction.

This gives 14.7 g (77% of theory) of 3-(4-bromo-2-fluoro-5-methyl-phenyl)-6-trifluoromethyl-2,4(1H,3H)-pyrimidinedione of melting point 186° C.

Example (IV-2)

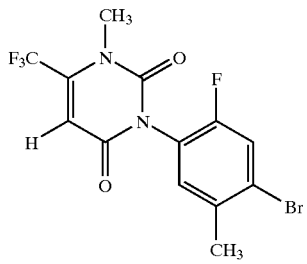

(Subsequent reaction)

A mixture of 19.4 g (53 mMol) of 3-(4-bromo-2-fluoro-5-methyl-phenyl)-6-trifluoromethyl-2,4 (1H,3H)-pyrimidinedione, 8.0 g (63 mMol) of dimethylsulphate, 11.0 g (79 mMol) of potassium carbonate and 100 ml of acetone is heated with stirring at reflux for 15 hours. The mixture is then concentrated under reduced pressure and the residue is taken up in ethyl acetate and washed with 1N hydrochloric acid. The aqueous phase is once more extracted with ethyl acetate. The combined organic phases are washed with water, dried with sodium sulphate and filtered off with suction through silica gel. The filtrate is concentrated under reduced pressure and the residue is purified by column chromatography—silica gel, chloroform/ethyl acetate (vol.: 2:1).

This gives 10.0 g (50% of theory) of 3-(4-bromo-2-fluoro-5-methyl-phenyl)-1-methyl-6-trifluoromethyl-2,4(1H,3H)-pyrimidinedione.

$^1$H-NMR (DMSO-D$_6$, δ): 6.56 ppm.

Example (IV-3)

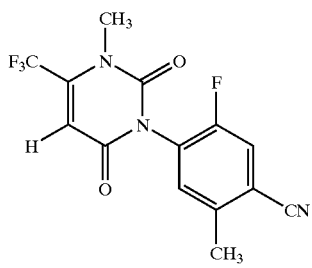

(Subsequent reaction)

2.10 g (5.5 mMol) of 3-(4-bromo-2-fluoro-5-methyl-phenyl)-1-methyl-6-trifluoromethyl-2,4 (1H,3H)-pyrimidinedione are initially charged in 5 ml of N,N-dimethylformamide and, under argon, heated at 160° C. for 30 minutes, using a water separator. At about 70° C., 0.57 g (6.3 mMol) of copper(I) cyanide are added, and the reaction mixture is stirred at 150° C. for 5 hours and at room temperature (about 20° C.) for another 18 hours. The mixture is then concentrated under reduced pressure and the residue is mixed with 1.34 g of iron(III) chloride and 50 ml of water. The mixture is acidified with 1N hydrochloric acid and then stirred at room temperature for 30 minutes. The mixture is then extracted with ethyl acetate and the organic phase is washed with water and with saturated aqueous sodium chloride solution, dried with sodium sulphate and filtered. The filtrate is concentrated under reduced pressure, the residue is digested with diethyl ether and the resulting crystalline product is isolated by filtration with suction.

This gives 1.08 g (60% of theory) of 5-fluoro-2-methyl-4-(3-methyl-2,6-dioxo-4-trifluoromethyl-3,6-dihydro-1(2H)-pyrimidinyl)-benzonitrile of melting point 186° C.

$^1$H-NMR (DMSO-D$_6$, δ): 6.60 ppm.

Starting materials of the formula (VII):

Example (VII-1)

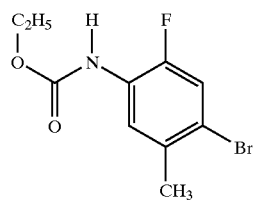

A mixture of 15.0 g (74 mMol) of 4-bromo-2-fluoro-5-methyl-aniline, 9.5 g (88 mMol) of ethyl chloroformate, 11.6 g of pyridine and 500 ml of methylene chloride is stirred at room temperature (about 20° C.) for 2 hours. Another 0.5 ml of ethyl chloroformate are added, and the mixture is stirred for another hour. The mixture is then washed with 1N hydrochloric acid, dried with sodium sulphate and filtered. From the filtrate, the solvent is carefully distilled off under reduced pressure.

This gives 14.4 g (70% of theory) of O-ethyl N-(4-bromo-2-fluoro-5-methyl-phenyl)-carbamate as an oily residue.

$^1$H-NMR (DMSO-D$_6$, δ): 7.61+7.63 ppm (d).

Starting Materials of the Formula (VIII):

Example (VIII-1)

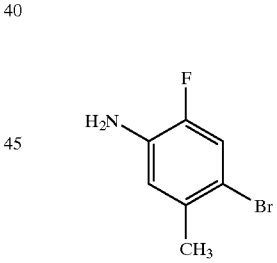

13.5 g (108 mMol) of 2-fluoro-5-methyl-aniline are initially charged in a mixture of 1 liter of methylene chloride and 400 ml of methanol, and 20 g of calcium carbonate (powder)—a little at a time—and a solution of 44.6 g (110 mMol) of benzyltrimethylammonium tribromide and 250 ml of methylene chloride/methanol (vol.: 5:2)—dropwise—are added successively with stirring. The mixture is stirred until the orange colour has disappeared. The mixture is then filtered, the filtrate is concentrated under reduced pressure using a rotary evaporator and the residue is admixed with 200 ml of water and extracted repeatedly with methyl t-butylether. The combined organic phases are dried with magnesium sulphate and filtered. The filtrate is concentrated under reduced pressure and the residue is crystallised using cyclohexane.

This gives 12.0 g (55% of theory) of 4-bromo-2-fluoro-5-methyl-aniline of melting point 57° C.

USE EXAMPLES

Example A

Pre-Emergence Test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of the solvent, the stated amount of emulsifier is added and the concentrate is diluted with water to the desired concentration.

Seeds of the test plants are sown in normal soil. After 24 hours, the soil is sprayed with the preparation of active compound such that the particular amount of active compound desired is applied per unit area. The concentration of active compound in the spray liquor is chosen such that the particular amount of active compound desired is applied in 1000 liters of water per hectare.

After three weeks, the degree of damage to the plants is rated in % damage in comparison to the development of the untreated controls. The figures denote:

0% = no effect (like untreated control)

100% = total destruction

In this test, for example, the compounds of Preparation Examples 3, 4, 6, 7, 8, 9, 12, 13, 16, 17, 18 and 19 exhibit very strong activity against weeds, and some of them are tolerated well by crop plants, such as, for example, maize.

Example B

Post-Emergence Test

| Solvent: | 5 parts by weight of acetone |
|---|---|
| Emulsifier: | 1 part by weight alkylaryl polyglycol ether |

To produce a suitable preparation of active compound, 1 part by weight of active compound is mixed with the stated amount of the solvent, the stated amount of emulsifier is added and the concentrate is diluted with water to the desired concentration.

Test plants of a height of 5–15 cm are sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:

0% = no effect (like untreated control)

100% = total destruction

In this test, for example, the compounds of Preparation Examples 2, 3, 4, 5, 6, 7, 8, 9, 10, 11, 12, 13, 16, 17, 18 and 19 exhibit very strong activity against weeds, and some are tolerated well by crop plants, such as, for example, maize and wheat.

What is claimed is:

1. A compound of formula (I)

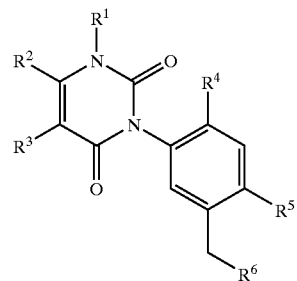

or a tautomeric form thereof or a salt or an acid or base adduct thereof, in which $R^1$ represents hydrogen, amino optionally cyano-, halogen-, or $C_1$–$C_4$-alkoxy-substituted alkyl having 1 to 4 carbon atoms, or optionally halogen-substituted alkenyl or alkynyl having 2 to 4 carbon atoms, $R^2$ represents cyano, carboxy, carbamoyl, thiocarbamoyl, or optionally cyano-, halogen-, or $C_1$–$C_4$-alkoxy-substituted alkyl or alkoxycarbonyl having 1 to 4 carbon atoms, $R^3$ represents hydrogen, halogen, or optionally halogen-substituted alkyl having 1 to 4 carbon atoms, $R^4$ represents hydrogen, nitro, cyano, $C_1$–$C_4$-alkoxy, or halogen, $R^5$ represents cyano, thiocarbamoyl, halogen, or optionally halogen-substituted alkyl or alkoxy having 1 to 4 carbon atoms, and $R^6$ represents a 4- to 12-membered saturated or unsaturated monocyclic or bicyclic heterocyclic group attached to $R^6$ via N and containing 1 to 4 heteroatoms selected from the group consisting of nitrogen atoms, oxygen atoms, sulphur atoms, —SO-groups, —$SO_2$-groups, -CO-groups, and —CS-groups, wherein the heterocyclic group is optionally substituted by nitro, hydroxyl, mercapto, amino, cyano, carboxyl, carbamoyl, halogen, $C_1$–$C_4$-alkyl, cyano-$C_1$–$C_4$-alkyl, carboxy-$C_1$–$C_4$-alkyl, $C_1$–$C_4$-halogenoalkyl, $C_1$–$C_4$-alkoxy-$C_1$–$C_4$-alkyl, $C_1$–$C_4$-alkoxycarbonyl-$C_1$–$C_4$-alkyl, $C_1$–$C_4$-alkylaminocarbonyl-$C_1$–$C_4$-alkyl, di($C_1$–$C_4$-alkyl)aminocarbonyl-$C_1$–$C_4$-alkyl, $C_1$–$C_4$-alkylcarbonyl, $C_1$–$C_4$-halogenoalkylcarbonyl, $C_1$–$C_4$-alkoxy-$C_1$–$C_4$-alkylcarbonyl, $C_1$–$C_4$-alkoxy, cyano-$C_1$–$C_4$-alkoxy, $C_1$–$C_4$-halogenoalkoxy, $C_1$–$C_4$-alkoxy-$C_1$–$C_4$alkoxy, carboxy-$C_1$–$C_4$-alkoxy, $C_1$–$C_4$-alkoxycarbonyl-$C_1$–$C_4$-alkoxy, $C_1$–$C_4$-alkylaminocarbonyl-$C_1$–$C_4$-alkoxy, di($C_1$–$C_4$-alkyl)aminocarbonyl-$C_1$–$C_4$-alkoxy, $C_2$–$C_4$-alkenyloxy, $C_2$–$C_4$-alkynyloxy, $C_1$–$C_4$-alkylthio, $C_1$–$C_4$-halogenoalkylthio, $C_1$–$C_4$-alkylsulphinyl, $C_1$–$C_4$-halogenoalkylsulphinyl, $C_1$–$C_4$-alkylsulphonyl, $C_1$–$C_4$-halogenoalkylsulphonyl, $C_1$–$C_4$-alkylcarbonylamino, $C_1$–$C_4$-alkoxycarbonyl-amino, $C_1$–$C_4$-alkylsulphonylamino, $C_2$–$C_4$-alkenyl, $C_2$–$C_4$-halogenoalkenyl, $C_2$–$C_4$-alkynyl, $C_2$–$C_4$-alkenyloxy, $C_2$–$C_4$-halogenoalkenyloxy, $C_2$–$C_4$alkynyl-oxy, $C_2$–$C_4$-alkenylthio, $C_2$–$C_4$-halogenoalkenylthio, $C_2$–$C_4$-alkynylthio, $C_2$–$C_4$-alkenylamino, $C_2$–$C_4$-alkynylamino; by optionally halogen-substituted $C_3$–$C_6$-cycloalkyl, $C_3$–$C_6$-Cycloalkyloxy, $C_3$–$C_6$-Cycloalkylthio, $C_3$–$C_6$-cycloalkylamino, $C_3$–$C_6$-cycloalkyl-$C_1$–$C_4$-alkyl, $C_3C_6$-cycoalkyl-$C_1$–$C_4$-alkyloxy, $C_3$–$C_6$-cycloalkyl-$C_1$–$C_4$-alkylthio, $C_3$–$C_6$-cycloalkyl-$C_1$–$C_4$-alkylamino; or by optionally nitro-, cyano-, halogen-, $C_1$–$C_4$-alkyl-, $C_1$–$C_4$-halogenoalkyl-, $C_1$–$C_4$-alkoxy-, or $C_1$–$C_4$-halogenoalkoxy-substituted phenyl, pyridyl, phenyloxy, phenylthio, phenyl-amino, benzyl, benzyloxy, benzylthio, or benzylamino.

2. A compound of formula (I) according to claim 1 wherein $R^1$ represents hydrogen, amino, optionally cyano-, fluorine-, chlorine-, methoxy-, or ethoxy-substituted methyl, ethyl, or n- or i-propyl, or optionally fluorine- and/or chlorine-substituted propenyl, butenyl, propynyl, or butynyl, $R^2$ represents cyano, carboxyl, carbamoyl, thiocarbamoyl, or optionally cyano-, fluorine-, chlorine-, methoxy-, or ethoxy-substituted methyl, ethyl, n- or i-propyl, methoxycarbonyl, ethoxycarbonyl, or n- or i-propoxycarbonyl, $R^3$ represents hydrogen, fluorine, chlorine, bromine, or optionally fluorine- and/or chlorine-substituted methyl, ethyl, or n- or i-propyl, $R^4$ represents hydrogen, methoxy, ethoxy, nitro, cyano, fluorine, chlorine, or bromine, $R^5$ represents cyano, thiocarbamoyl, fluorine, chlorine, bromine, or optionally fluorine- or chlorine-substituted methyl, ethyl, n- or i-propyl, methoxy, ethoxy, or n- or i-propoxy, and $R^6$ represents saturated or unsaturated monocyclic or bicyclic nitrogen-containing heterocyclic group attached to $R^6$ via N and selected from the group consisting of pyrrolyl, pyrrolidinyl, pyrazolyl, imidazolyl, isoxazolidinyl, triazolyl, piperidinyl, morpholinyl, thiomorpholinyl, and piperazinyl, wherein the heterocyclic group is optionally substituted by nitro, hydroxyl, mercapto, amino, cyano, carboxyl, carbamoyl, fluorine, chlorine, bromine, iodine, methyl, ethyl, n- or i-propyl, n-, i-, s-, or t-butyl, cyanomethyl, cyanoethyl, cyano-n-propyl, cyano-i-propyl, carboxymethyl, carboxyethyl, carboxy-n-propyl, carboxy-i-propyl, fluoromethyl, chloromethyl, bromomethyl, difluoromethyl, dichloromethyl, trifluoromethyl, trichloromethyl, fluorodichloromethyl, chlorodifluoromethyl, fluoroethyl, chloroethyl, difluoroethyl, dichloroethyl, chlorofluoroethyl, trifluoroethyl, trichloroethyl, fluorodichloroethyl, chlorodifluoroethyl, tetrafluoroethyl, chlorotrifluoroethyl, dichlorodifluoroethyl, pentafluoroethyl, methoxymethyl, ethoxymethyl, n- or i-propoxymethyl, methoxyethyl, ethoxyethyl, n- or i-propoxyethyl, methoxypropyl, ethoxypropyl, methoxycarbonylmethyl, ethoxycarbonylmethyl, n- or i-propoxycarbonylmethyl, methoxycarbonylethyl, ethoxycarbonylethyl, n- or i-propoxycarbonylethyl, methoxycarbonylpropyl, ethoxycarbonylpropyl, methylaminocarbonylmethyl, ethylaminocarbonylmethyl, n- or i-propylaminocarbonylmethyl, methylaminocarbonylethyl, ethylaminocarbonylethyl, n- or i-propylaminocarbonylethyl, dimethylaminocarbonylmethyl, dimethylaminocarbonylethyl, acetyl, propionyl, n- or i-butyroyl, trifluoroacetyl, chloroacetyl, dichloroacetyl, trichloroacetyl, methoxyacetyl, ethoxyacetyl, methoxy, ethoxy, n- or i-propoxy, cyanomethoxy, cyanoethoxy, cyano-n-propoxy, cyano-i-propoxy, fluoromethoxy, difluoromethoxy, trifluoromethoxy, fluorodichloromethoxy, chlorodifluoromethoxy, fluoroethoxy, chloroethoxy, difluoroethoxy, dichloroethoxy, chlorofluoroethoxy, trifluoroethoxy, trichloroethoxy, fluorodichloroethoxy, chlorodifluoroethoxy, methoxymethoxy, ethoxymethoxy, n- or i-propoxymethoxy, methoxyethoxy, ethoxyethoxy, n- or i-propoxyethoxy, carboxymethoxy, carboxyethoxy, methoxycarbonylmethoxy, ethoxycarbonylmethoxy, n- or i-propoxycarbonylmethoxy, methoxycarbonylethoxy, ethoxycarbonylethoxy, n- or i-propoxycarbonylethoxy, methylaminocarbonylmethoxy, ethylaminocarbonylmethoxy, n- or i-propylaminocarbonylmethoxy, methylaminocarbonylethoxy, ethylaminocarbonylethoxy, n- or i-propylaminocarbonylethoxy, dimethylaminocarbonylmethoxy, dimethylaminocarbonylethoxy, methoxycarbonyl, ethoxycarbonyl, n- or i-propoxycarbonyl, propenyloxy, butenyloxy, propynyloxy, butynyloxy, methylthio, ethylthio, n- or i-propylthio, difluoromethylthio, trifluoromethylthio, fluorodichloromethylthio, chlorodifluoromethylthio, methylsulphinyl, ethylsulphinyl, n- or i-propylsulphinyl, trifluoromethylsulphinyl, methylsulphonyl, ethylsulphonyl, n- or i-propylsulphonyl, trifluoromethylsulphonyl; by optionally fluorine-, chlorine-, methoxy-, or ethoxy-substituted acetylamino, propionylamino, n- or i-butyroylamino, methoxycarbonylamino, ethoxycarbonylamino, or n- or i-propoxycarbonylamino; by optionally fluorine- and/or chlorine-substituted methylsulphonylamino-, ethylsulphonylamino-, or n- or i-propylsulphonylamino; by optionally fluorine- and/or chlorine-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino, or cyclohexylmethylamino; or by optionally nitro-, cyano-, fluorine-, chlorine-, bromine-, methyl-, ethyl-, n- or i-propyl-, n-, i-, s-, or t-butyl-, trifluoromethyl-, methoxy-, ethoxy-, n- or i-propoxy-, difluoromethoxy-, or trifluoromethoxy-substituted phenyl, pyridyl, phenyloxy, phenylthio, phenylamino, benzyl, benzyloxy, benzylthio, or benzylamino; or represents one of the groups

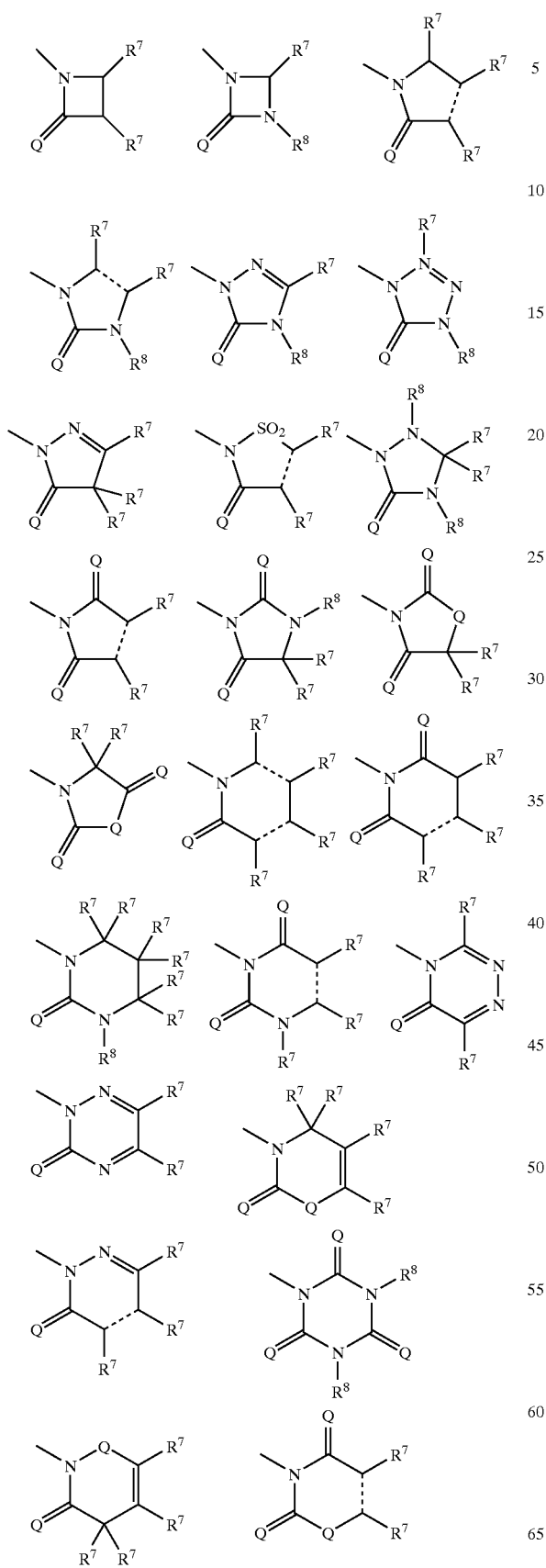
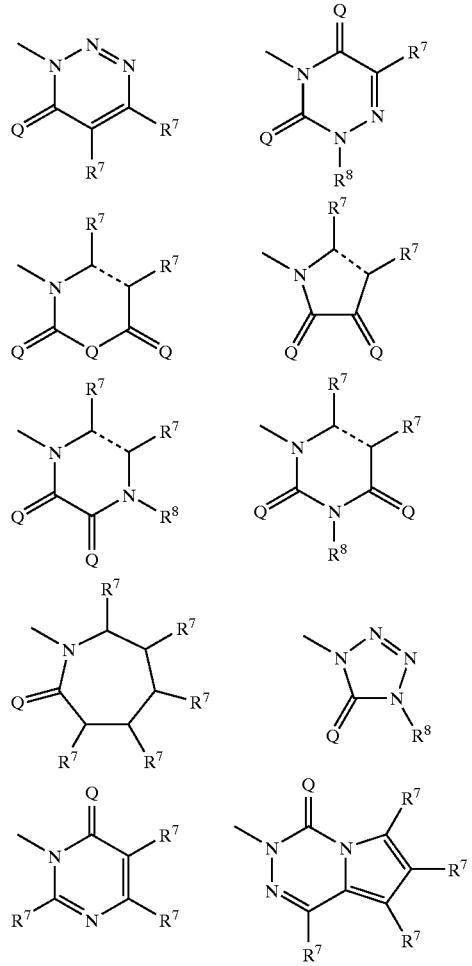

where
a dashed line represents either a single bond or a double bond,

Q represents oxygen or sulphur, $R^7$ represents hydrogen, hydroxyl, mercapto, cyano, fluorine, chlorine, bromine, or iodine; represents optionally fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl-, ethylsulphonyl-, or n- or i-propylsulphonyl-substituted methyl, ethyl, n- or i-propyl, n-, i-, s-, or t-butyl, methoxy, ethoxy, n- or i-propoxy, n-, i-, s-, or t-butoxy, methylthio, ethylthio, n- or i-propylthio, n-, i-, s-, or t-butylthio, methylsulphinyl, ethylsulphinyl, n- or i-propylsulphinyl, methylsulphonyl, ethylsulphonyl, or n- or i-propylsulphonyl; represents methylamino, ethylamino, n- or i-propylamino, n-, i-, s-, or t-butylamino, dimethylamino, diethylamino, di-n-propylamino, or di-i-propylamino; represents optionally fluorine- and/or chlorine-substituted ethenyl, propenyl, butenyl, ethynyl, propynyl, butynyl, propenyloxy, butenyloxy, propenylthio, butenylthio, propenylamino, or butenylamino; represents optionally fluorine- and/or chlorine-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino, or cyclohexyl-methylamino; or represents optionally fluorine-, chlorine-, methyl-, ethyl-, n- or i-propyl-, n-, i-, s-, or t-butyl-, methoxy-, ethoxy-, or n- or i-propoxy-substituted phenyl, phenyloxy, phenylthio, phenylamino, benzyl, benzyloxy, benzylthio, or benzylamino, and $R^8$ represents hydrogen, hydroxyl, or amino; represents optionally fluorine- and/or chlorine-, methoxy-, or ethoxy-substituted methyl, ethyl, n- or i-propyl, n-, i-, or s-butyl, methoxy, ethoxy, n- or i-propoxy, methylamino, ethylamino, or dimethylamino; represents optionally fluorine- and/or chlorine-substituted ethenyl, propenyl, ethynyl, propynyl, or propenyloxy; represents optionally fluorine- and/or chlorine-substituted cyclopropyl, cyclobutyl, cyclopentyl, cyclohexyl, cyclopropylmethyl, cyclobutylmethyl, cyclopentylmethyl, or cyclohexylmethyl; or represents optionally fluorine-, chlorine- methyl-, ethyl-, n- or i-propyl-, n-, i-, s-, or t-butyl-, methoxy-, ethoxy-, or n- or i-propoxy-substituted phenyl or benzyl.

3. A compound of formula (I) according to claim 1 wherein $R^1$ represents hydrogen, amino, or methyl, $R^2$ represents cyano, carboxyl, carbamoyl, or thiocarbamoyl; represents optionally fluorine- and/or chlorine-substituted methyl or ethyl; or represents methoxycarbonyl or ethoxycarbonyl, $R^3$ represents hydrogen, fluorine, chlorine, or bromine; or represents optionally fluorine- and/or chlorine-substituted methyl, $R^4$ represents hydrogen, fluorine, or chlorine, $R^5$ represents cyano, thiocarbamoyl, chlorine, or bromine; or represents optionally fluorine- and/or chlorine-substituted methyl or methoxy, $R^6$ represents a saturated or unsaturated monocyclic or bicyclic nitrogen-containing heterocyclic group attached to $R^6$ via N and selected from the group consisting of pyrrolyl, pyrrolidinyl, pyrazolyl, imidazolyl, isoxazolidinyl, triazolyl, piperidinyl, morpholinyl, thiomorpholinyl, or piperazinyl, wherein the heterocyclic group is optionally substituted by nitro, hydroxyl, mercapto, amino, cyano, carboxyl, carbamoyl, fluorine, chlorine, bromine, iodine, methyl, ethyl, n- or i-propyl, n-, i-, s-, or t-butyl, cyanomethyl, cyanoethyl, cyano-n-propyl, cyano-i-propyl, carboxymethyl, carboxyethyl, carboxy-n-propyl, carboxy-i-propyl, fluoromethyl, chloromethyl, bromomethyl, difluoromethyl, dichloromethyl, trifluoromethyl, trichloromethyl, fluorodichloromethyl, chlorodifluoromethyl, fluoroethyl, chloroethyl, difluoroethyl, dichloroethyl, chlorofluoroethyl, trifluoroethyl, trichloroethyl, fluorodichloroethyl, chlorodifluoroethyl, tetrafluoroethyl, chlorotrifluoroethyl, dichlorodifluoroethyl, pentafluoroethyl, methoxymethyl, ethoxymethyl, n- or i-propoxymethyl, methoxyethyl, ethoxyethyl, n- or i-propoxyethyl, methoxypropyl, ethoxypropyl, methoxycarbonylmethyl, ethoxycarbonylmethyl, n- or i-propoxycarbonylmethyl, methoxycarbonylethyl, ethoxycarbonylethyl, n- or i-propoxycarbonylethyl, methoxycarbonylpropyl, ethoxycarbonylpropyl, methylaminocarbonylmethyl, ethylaminocarbonylmethyl, n- or i-propylaminocarbonylmethyl, methylaminocarbonylethyl, ethylaminocarbonylethyl, n- or i-propylaminocarbonylethyl, dimethylaminocarbonylmethyl, dimethylaminocarbonylethyl, methoxy, ethoxy, n- or i-propoxy, cyanomethoxy, cyanoethoxy, cyano-n-propoxy, cyano-i-propoxy, fluoromethoxy, difluoromethoxy, trifluoromethoxy, fluorodichloromethoxy, chlorodifluoromethoxy, fluoroethoxy, chloroethoxy, difluoroethoxy, dichloroethoxy, chlorofluoroethoxy, trifluoroethoxy, trichloroethoxy, fluorodichloroethoxy, chlorodifluoroethoxy, methoxymethoxy, ethoxymethoxy, n- or i-propoxymethoxy, methoxyethoxy, ethoxyethoxy, n- or i-propoxyethoxy, carboxymethoxy, carboxyethoxy, methoxycarbonylmethoxy, ethoxycarbonylmethoxy, n- or i-propoxycarbonylmethoxy, methoxycarbonylethoxy, ethoxycarbonylethoxy, n- or i-propoxycarbonylethoxy, methylaminocarbonylmethoxy, ethylaminocarbonylmethoxy, n- or i-propylaminocarbonylmethoxy, methylaminocarbonylethoxy, ethylaminocarbonylethoxy, n- or i-propylaminocarbonylethoxy, dimethylaminocarbonylmethoxy, dimethylaminocarbonylethoxy, propenyloxy, butenyloxy, propynyloxy, butynyloxy, methylthio, ethylthio, n- or i-propylthio, difluoromethylthio, trifluoromethylthio, fluorodichloromethylthio, chlorodifluoromethylthio, methylsulphinyl, ethylsulphinyl, n- or i-propylsulphinyl, trifluoromethylsulphinyl, methylsulphonyl, ethylsulphonyl, n- or i-propylsulphonyl, or trifluoromethylsulphonyl; by optionally fluorine-, chlorine-, methoxy-, or ethoxy-substituted acetylamino, propionylamino, n- or i-butyroylamino, methoxycarbonylamino, ethoxycarbonylamino, or n- or i-propoxycarbonylamino; by optionally fluorine- and/or chlorine-substituted methylsulphonylamino, ethylsulphonylamino, or n- or i-propylsulphonylamino; by optionally fluorine- and/or chlorine-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino, or cyclohexylmethylamino; or by optionally nitro-, cyano-, fluorine-, chlorine-, bromine-, methyl-, ethyl-, n- or i-propyl-, n-, i-, s-, or tbutyl-, trifluoromethyl-, methoxy-, ethoxy-, n- or i-propoxy-, difluoromethoxy-, or trifluoromethoxy-substituted phenyl, phenyloxy, phenylthio, phenylamino, benzyl, benzyloxy, benzylthio, or benzylamino, or represents one of the groups

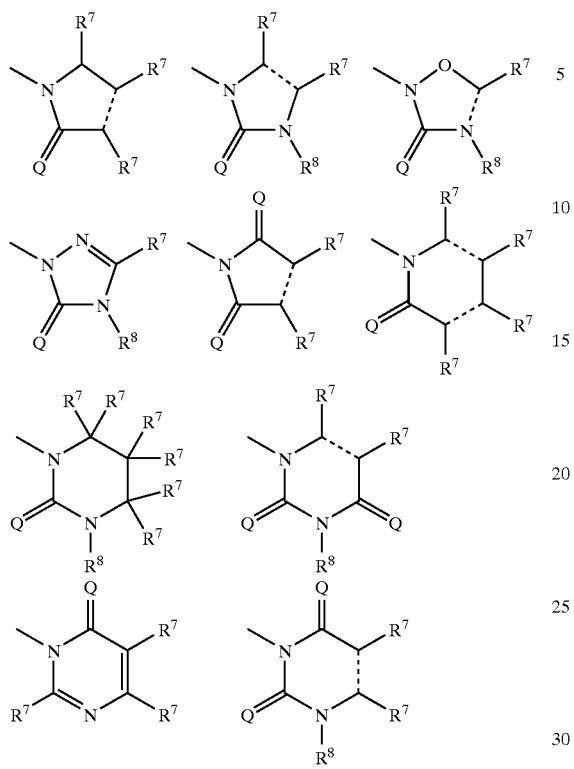

where a dashed line represents either a single bond or a double bond,

Q represents oxygen,

R$^7$ represents hydrogen, hydroxyl, mercapto, cyano, fluorine, or chlorine; represents optionally fluorine-, chlorine-, methoxy-, ethoxy-, methylthio-, or ethylthio-substituted methyl, ethyl, methoxy, ethoxy, or methylthio; represents methylamino, ethylamino, dimethylamino, or diethylamino; represents optionally fluorine- and/or chlorine-substituted cyclopropyl, cyclobutyl, cyclopentyl, cyclohexyl, cyclopropyloxy, cyclobutyloxy, cyclopentyloxy, or cyclohexyloxy; or represents optionally fluorine-, chlorine-, methyl-, ethyl-, methoxy-, or ethoxy-substituted phenyl, phenyloxy, benzyl, or benzyloxy, and R$^8$ represents hydrogen, hydroxyl, or amino; represents optionally fluorine- and/or chlorine-, methoxy-, or ethoxy-substituted methyl, ethyl, methoxy, ethoxy, methylamino, ethylamino, or dimethylamino; represents optionally fluorine- and/or chlorine-substituted cyclopropyl, cyclobutyl, cyclopentyl, cyclohexyl, cyclopropylmethyl, cyclobutylmethyl, cyclopentylmethyl, or cyclohexylmethyl; or represents optionally fluorine-, chlorine- methyl-, ethyl-, methoxy-, or ethoxy-substituted phenyl or benzyl.

4. A compound of formula (I) according to claim 1 wherein

R$^2$ represents fluorine- and/or chlorine-substituted methyl or ethyl, or represents methoxycarbonyl or ethoxycarbonyl, R$^3$ represents hydrogen, fluorine, or chlorine, or represents optionally fluorine- and/or chlorine-substituted methyl, R$^5$ represents cyano, chlorine, or bromine, and R$^6$ represents a heterocyclic group attached to R$^6$ via N and selected from the group consisting of pyrrolidinyl, isoxazolidinyl, piperidinyl, morpholinyl, thiomorpholinyl, and piperazinyl, wherein the heterocyclic group is optionally substituted by hydroxyl, amino, fluorine, chlorine, methyl, ethyl, trifluoromethyl, methylthio, ethylthio, methylamino, dimethylamino, diethylamino, cyclopropyl, cyclobutyl, cyclopentyl, or cyclohexyl, or represents one of the groups

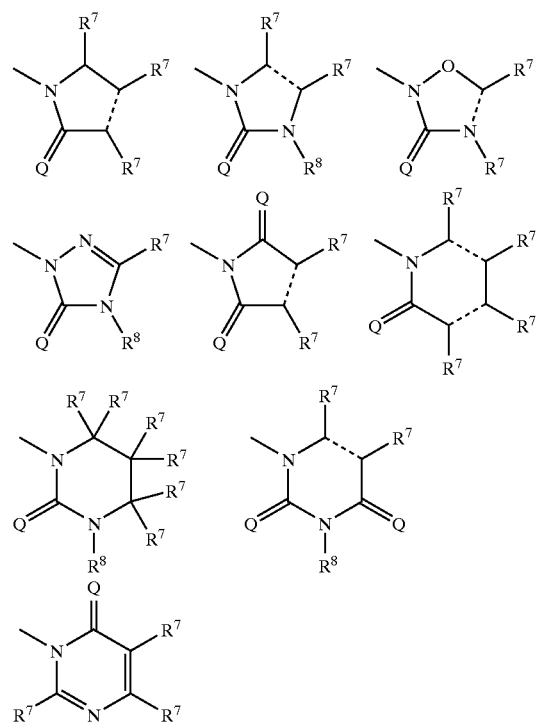

where a dashed line represents either a single bond or a double bond,

Q represents oxygen,

R$^7$ represents hydrogen, hydroxyl, mercapto, cyano, fluorine, or chlorine; represents optionally fluorine-, chlorine-, methoxy-, ethoxy-, methylthio-, or ethylthio-substituted methyl, ethyl, methoxy, ethoxy, or methylthio; represents methylamino, ethylamino, dimethylamino, or diethylamino; represents optionally fluorine- and/or chlorine-substituted cyclopropyl, cyclobutyl, cyclopentyl, cyclohexyl, cyclopropyloxy, cyclobutyloxy, cyclopentyloxy, or cyclohexyloxy; or represents optionally fluorine-, chlorine-, methyl-, ethyl-, methoxy-, or ethoxy-substituted phenyl, phenyloxy, benzyl, or benzyloxy, and R$^8$ represents hydrogen, hydroxyl, or amino; represents optionally fluorine- and/or chlorine-, methoxy-, or ethoxy-substituted methyl, ethyl, methoxy, ethoxy, methylamino, ethylamino, or dimethylamino; represents optionally fluorine- and/or chlorine-substituted cyclopropyl, cyclobutyl, cyclopentyl, cyclohexyl, cyclopropylmethyl, cyclobutylmethyl, cyclopentyl-methyl, or cyclohexylmethyl; or represents optionally fluorine-, chlorine- methyl-, ethyl-, methoxy-, or ethoxy-substituted phenyl or benzyl.

5. A compound of formula (I) according to claim 1 wherein $R^1$ represents hydrogen, amino, or methyl,
$R^2$ represents cyano or trifluoromethyl,
$R^3$ represents hydrogen, fluorine, chlorine, or methyl,
$R^4$ represents hydrogen, fluorine, or chlorine,
$R^5$ represents cyano, thiocarbamoyl, chlorine, or bromine,
$R^6$ represents the group

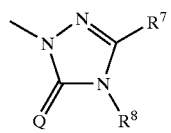

where represents oxygen, $R^7$ represents hydrogen, chlorine, bromine, or iodine; represents optionally fluorine-, chlorine-, methoxy-, ethoxy-, methylthio-, ethylthio-, methylsulphinyl-, ethylsulphinyl-, methylsulphonyl-, or ethylsulphonyl-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, or ethylsulphonyl; represents methylamino, ethylamino, n- or i-propylamino, dimethylamino, or diethylamino; represents optionally fluorine- and/or chlorine-substituted ethenyl, propenyl, ethynyl, propynyl, propenyloxy, propenylthio, or propenylamino; represents optionally fluorine- and/or chlorine-substituted cyclopropyl; or represents optionally fluorine-, chlorine-, methyl-, ethyl-, methoxy-, or ethoxy-substituted phenyl, phenyloxy, phenylthio, phenylamino, benzyl, benzyloxy, benzylthio, or benzylamino, and $R^8$ represents hydrogen or amino; represents optionally fluorine- and/or chlorine-, methoxy-, or ethoxy-substituted methyl, ethyl, n- or i-propyl, methoxy, ethoxy, or n- or i-propoxy; represents optionally fluorine- and/or chlorine-substituted cyclopropyl; or represents optionally fluorine- or chlorine-, methyl-, ethyl-, methoxy-, or ethoxy-substituted phenyl or benzyl.

6. A sodium, potassium, magnesium, calcium, ammonium, $C_1$–$C_4$-alkyl-ammonium, di($C_1$–$C_4$-alkyl)ammonium, tri($C_1$–$C_4$alkyl)ammonium, tetra($C_1$–$C_4$-alkyl)ammonium, tri($C_1$–$C_4$-alkyl)sulphonium-, $C_5$— or $C_6$-cycloalkyl-ammonium, or di($C_1$–$C_2$-alkyl)benzylammonium salt or a metal complex of a compound of formula (I) according to claim 1.

7. A metal complex of a compound of formula (I) according to claim 6 wherein the metal is copper, iron, cobalt, or nickel.

8. A process for preparing a compound of formula (I) according to claim 1 comprising reacting a compound of formula (II)

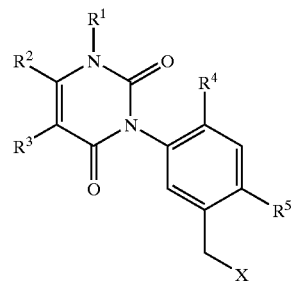

in which
$R^1$ represents hydrogen, amino, or optionally substituted alkyl, alkenyl, or alkynyl,
$R^2$ represents cyano, carboxy, carbamoyl, thiocarbamoyl, or optionally substituted alkyl or alkoxycarbonyl,
$R^3$ represents hydrogen, halogen, or optionally substituted alkyl,
$R^4$ represents hydrogen, nitro, cyano, alkoxy, or halogen,
$R^5$ represents cyano, thiocarbamoyl, halogen, or optionally substituted alkyl or alkoxy, and
X represents halogen,
with a nitrogen heterocycle of formula (III)

$$H\text{—}R^6 \qquad (III)$$

in which $R^6$ represents an optionally substituted nitrogen-containing
heterocyclic group attached to $R^6$ via N,
optionally in the presence of one or more reaction auxiliaries and optionally in the presence of one or more diluents.

9. A process according to claim 8 additionally comprising converting the resulting compound of formula (I) into another compound of formula (I) within the scope of the definition of the substituents.

10. A process according to claim 9 carried out by an electrophilic or nucleophilic substitution reaction or by an oxidation or reduction reaction.

11. A crop treatment composition comprising an effective amount of one or more compounds of formula (I) according to claim 1 and customary extenders.

12. A method for controlling undesirable plants comprising allowing an effective amount of one or more compounds of formula (I) according to claim 1 to act on the undesirable plants and/or their habitat.

13. A method for controlling undesirable plants comprising allowing an effective amount of one or more compositions according to claim 11 to act on the undesirable plants and/or their habitat.

14. A process for preparing a herbicidal composition comprising mixing a compound of formula (I) according to claim 1 with extenders and/or surfactants.

* * * * *